(12) United States Patent
Kleiner

(10) Patent No.: US 8,870,882 B2
(45) Date of Patent: Oct. 28, 2014

(54) APPARATUS AND METHOD OF SPINAL IMPLANT AND FUSION

(71) Applicant: Jeffrey Kleiner, Aurora, CO (US)

(72) Inventor: Jeffrey Kleiner, Aurora, CO (US)

( * ) Notice: Subject to any disclaimer, the term of this patent is extended or adjusted under 35 U.S.C. 154(b) by 0 days.

(21) Appl. No.: 13/754,042

(22) Filed: Jan. 30, 2013

(65) Prior Publication Data

US 2013/0338720 A1  Dec. 19, 2013

Related U.S. Application Data

(63) Continuation of application No. 12/632,720, filed on Dec. 7, 2009, now Pat. No. 8,366,748.

(60) Provisional application No. 61/120,260, filed on Dec. 5, 2008, provisional application No. 61/186,683, filed on Jun. 12, 2009.

(51) Int. Cl.
| | | |
|---|---|---|
| A61B 17/58 | (2006.01) | |
| A61B 17/16 | (2006.01) | |
| A61B 17/064 | (2006.01) | |
| A61B 17/86 | (2006.01) | |
| A61B 17/84 | (2006.01) | |
| A61B 17/70 | (2006.01) | |
| A61B 17/02 | (2006.01) | |
| A61B 17/92 | (2006.01) | |
| A61B 17/34 | (2006.01) | |
| A61B 17/00 | (2006.01) | |

(52) U.S. Cl.
CPC ....... *A61B 17/7082* (2013.01); *A61B 2017/922* (2013.01); *A61B 17/1659* (2013.01); *A61B 2017/3433* (2013.01); *A61B 17/0642* (2013.01); *A61B 17/864* (2013.01); *A61B 2017/00004* (2013.01); *A61B 17/846* (2013.01); *A61B 17/1671* (2013.01); *A61B 17/7064* (2013.01); *A61B 17/025* (2013.01); *A61B 17/3421* (2013.01); *A61B 2017/0256* (2013.01)
USPC ............................ 606/86 A; 606/246; 606/99

(58) Field of Classification Search
USPC .......................... 606/99, 86 A, 246–249, 279
See application file for complete search history.

(56) References Cited

U.S. PATENT DOCUMENTS

| | | |
|---|---|---|
| D30,951 S | 6/1899 | Saint Cyr, Jr. |
| 1,867,624 A | 7/1932 | Hoffman |

(Continued)

FOREIGN PATENT DOCUMENTS

| | | |
|---|---|---|
| WO | WO 99/08627 | 2/1999 |
| WO | WO 2005/037149 | 4/2005 |

OTHER PUBLICATIONS

U.S. Appl. No. 13/168,611, filed Jun. 24, 2011, Kleiner.

(Continued)

*Primary Examiner* — Jerry Cumberledge
*Assistant Examiner* — Tara Carter
(74) *Attorney, Agent, or Firm* — Sheridan Ross P.C.

(57) ABSTRACT

An apparatus and method of performing a minimally invasive posterior spine fusion. More specifically an apparatus with a handle and a forked head on the distal end of the handle is used to grasp implant material and introduce the material to an implant site. The shaft of the apparatus is shaped so as to allow the affixation of a drill guide and drill while simultaneously holding the implant material in the implant site. After removal of the boring tools and assembly of the fusing element, the apparatus can be selectively removed from the implant site. A method of achieving facet joint fusion with near simultaneous fixation is also disclosed.

14 Claims, 12 Drawing Sheets

(56) References Cited

U.S. PATENT DOCUMENTS

| | | |
|---|---|---|
| 2,520,464 A | 8/1950 | Hubner |
| 3,697,011 A | 10/1972 | Christensen et al. |
| 3,741,496 A | 6/1973 | Beller |
| 3,836,092 A | 9/1974 | Hull |
| 3,855,638 A | 12/1974 | Pilliar |
| 4,039,156 A | 8/1977 | Abraham |
| 4,041,939 A | 8/1977 | Hall |
| 4,047,524 A | 9/1977 | Hall |
| 4,206,516 A | 6/1980 | Pilliar |
| 4,277,184 A | 7/1981 | Solomon |
| 4,430,062 A | 2/1984 | Henrichsen et al. |
| 4,462,402 A | 7/1984 | Burgio et al. |
| 4,467,478 A | 8/1984 | Jurgutis |
| 4,501,269 A | 2/1985 | Bagby |
| 4,522,270 A | 6/1985 | Kishi |
| 4,570,623 A | 2/1986 | Ellison et al. |
| 4,580,978 A | 4/1986 | Motola et al. |
| 4,592,346 A | 6/1986 | Jurgutis |
| 4,743,256 A | 5/1988 | Brantigan |
| 4,877,399 A | 10/1989 | Frank et al. |
| 4,925,924 A | 5/1990 | Silver et al. |
| 4,991,570 A | 2/1991 | Bullard |
| 5,037,422 A | 8/1991 | Hayhurst |
| 5,053,038 A | 10/1991 | Sheehan |
| 5,055,104 A | 10/1991 | Ray |
| 5,058,823 A | 10/1991 | Emura et al. |
| 5,282,744 A | 2/1994 | Meyer |
| 5,290,295 A | 3/1994 | Querals et al. |
| 5,311,640 A | 5/1994 | Holland |
| 5,312,407 A | 5/1994 | Carter |
| 5,312,417 A | 5/1994 | Wilk |
| 5,324,307 A | 6/1994 | Jarrett et al. |
| 5,329,834 A | 7/1994 | Wong |
| 5,333,812 A | 8/1994 | Sato |
| D351,022 S | 9/1994 | Saito |
| 5,354,292 A | 10/1994 | Braeuer et al. |
| 5,395,372 A | 3/1995 | Holt et al. |
| D360,689 S | 7/1995 | Giampapa |
| 5,431,658 A | 7/1995 | Moskovich |
| 5,443,514 A * | 8/1995 | Steffee ............ 128/898 |
| D364,462 S | 11/1995 | Michelson |
| 5,520,611 A | 5/1996 | Rao et al. |
| D370,531 S | 6/1996 | Ash et al. |
| 5,527,312 A | 6/1996 | Ray |
| D372,311 S | 7/1996 | Koros et al. |
| D372,781 S | 8/1996 | Reif |
| 5,549,607 A | 8/1996 | Olson et al. |
| 5,554,191 A | 9/1996 | Lahille et al. |
| 5,558,674 A | 9/1996 | Heggeness et al. |
| D374,283 S | 10/1996 | Michelson |
| 5,562,661 A | 10/1996 | Yoshimi et al. |
| 5,569,246 A | 10/1996 | Ojima et al. |
| 5,586,989 A | 12/1996 | Bray |
| 5,595,563 A | 1/1997 | Moisdon |
| 5,601,557 A | 2/1997 | Hayhurst |
| D378,409 S | 3/1997 | Michelson |
| 5,611,800 A | 3/1997 | Davis et al. |
| 5,634,925 A | 6/1997 | Urbanski |
| 5,653,763 A | 8/1997 | Errico et al. |
| 5,662,655 A | 9/1997 | Laboureau et al. |
| 5,665,122 A | 9/1997 | Kambin |
| 5,683,464 A * | 11/1997 | Wagner et al. ............ 623/17.16 |
| 5,688,285 A | 11/1997 | Yamada |
| 5,697,932 A | 12/1997 | Smith et al. |
| 5,702,449 A | 12/1997 | McKay |
| 5,704,892 A | 1/1998 | Adair |
| 5,741,253 A | 4/1998 | Michelson |
| 5,762,629 A | 6/1998 | Kambin |
| 5,779,642 A | 7/1998 | Nightengale |
| 5,782,919 A | 7/1998 | Zdeblick et al. |
| 5,797,918 A | 8/1998 | McGuire et al. |
| 5,836,948 A | 11/1998 | Zucherman et al. |
| 5,836,958 A | 11/1998 | Ralph |
| 5,860,973 A | 1/1999 | Michelson |
| 5,860,977 A | 1/1999 | Zucherman et al. |
| 5,865,746 A | 2/1999 | Murugesan et al. |
| 5,865,846 A | 2/1999 | Bryan et al. |
| 5,871,462 A | 2/1999 | Yoder et al. |
| 5,888,228 A | 3/1999 | Knothe et al. |
| 5,904,689 A | 5/1999 | Jonjic |
| 5,904,718 A | 5/1999 | Jefferies |
| 5,906,616 A | 5/1999 | Pavlov et al. |
| 5,925,051 A | 7/1999 | Mikhail |
| 5,925,056 A | 7/1999 | Thomas et al. |
| 5,944,658 A | 8/1999 | Koros et al. |
| 5,944,686 A | 8/1999 | Patterson et al. |
| 5,947,972 A | 9/1999 | Gage et al. |
| 5,976,146 A | 11/1999 | Ogawa et al. |
| 5,989,257 A | 11/1999 | Tidwell et al. |
| 5,997,895 A | 12/1999 | Narotam et al. |
| 6,004,191 A | 12/1999 | Schur et al. |
| 6,004,326 A | 12/1999 | Castro et al. |
| 6,013,028 A | 1/2000 | Jho et al. |
| 6,019,765 A | 2/2000 | Thornhill et al. |
| 6,030,356 A | 2/2000 | Carlson et al. |
| 6,030,388 A | 2/2000 | Yoshimi et al. |
| 6,030,390 A | 2/2000 | Mehdizadeh |
| 6,030,401 A | 2/2000 | Marino |
| 6,033,408 A | 3/2000 | Gage et al. |
| 6,033,438 A | 3/2000 | Bianchi et al. |
| 6,045,555 A | 4/2000 | Smith et al. |
| 6,059,829 A | 5/2000 | Schlapfer et al. |
| 6,090,143 A | 7/2000 | Meriwether et al. |
| 6,096,080 A | 8/2000 | Nicholson et al. |
| 6,113,602 A | 9/2000 | Sand |
| 6,120,503 A | 9/2000 | Michelson |
| 6,123,705 A | 9/2000 | Michelson |
| 6,136,001 A | 10/2000 | Michelson |
| 6,142,998 A | 11/2000 | Smith et al. |
| 6,146,420 A | 11/2000 | McKay |
| 6,149,096 A | 11/2000 | Hartley |
| 6,152,871 A | 11/2000 | Foley et al. |
| 6,159,211 A | 12/2000 | Boriani et al. |
| 6,159,245 A | 12/2000 | Meriwether et al. |
| 6,180,085 B1 | 1/2001 | Achilefu |
| 6,209,886 B1 | 4/2001 | Estes et al. |
| 6,216,573 B1 | 4/2001 | Moutafis et al. |
| 6,224,599 B1 | 5/2001 | Baynham et al. |
| 6,235,805 B1 | 5/2001 | Chang et al. |
| 6,238,397 B1 | 5/2001 | Zucherman et al. |
| 6,241,733 B1 | 6/2001 | Nicholson et al. |
| 6,241,769 B1 | 6/2001 | Nicholson et al. |
| 6,245,108 B1 | 6/2001 | Biscup |
| 6,258,094 B1 | 7/2001 | Nicholson et al. |
| 6,261,293 B1 | 7/2001 | Nicholson et al. |
| 6,261,295 B1 | 7/2001 | Nicholson et al. |
| 6,261,296 B1 | 7/2001 | Aebi et al. |
| 6,290,724 B1 | 9/2001 | Marino |
| 6,299,613 B1 | 10/2001 | Ogilvie et al. |
| 6,309,395 B1 | 10/2001 | Smith et al. |
| 6,325,805 B1 | 12/2001 | Ogilvie et al. |
| 6,328,738 B1 | 12/2001 | Suddaby |
| 6,336,928 B1 | 1/2002 | Guerin et al. |
| 6,342,074 B1 | 1/2002 | Simpson |
| 6,364,880 B1 | 4/2002 | Michelson |
| 6,375,635 B1 | 4/2002 | Moutafis et al. |
| 6,387,096 B1 | 5/2002 | Hyde, Jr. |
| 6,409,765 B1 | 6/2002 | Bianchi et al. |
| 6,436,101 B1 | 8/2002 | Hamada |
| 6,447,512 B1 * | 9/2002 | Landry et al. ............ 606/86 A |
| 6,451,017 B1 | 9/2002 | Moutafis et al. |
| 6,454,806 B1 | 9/2002 | Cohen et al. |
| 6,467,556 B2 | 10/2002 | Alsruhe |
| D467,657 S | 12/2002 | Scribner |
| 6,500,206 B1 | 12/2002 | Bryan |
| 6,511,493 B1 | 1/2003 | Moutafis et al. |
| D469,871 S | 2/2003 | Sand |
| 6,520,976 B1 | 2/2003 | Gage |
| 6,524,318 B1 | 2/2003 | Longhini et al. |
| 6,565,574 B2 | 5/2003 | Michelson |
| 6,569,201 B2 | 5/2003 | Moumene et al. |
| 6,613,091 B1 | 9/2003 | Zdeblick et al. |
| 6,616,669 B2 | 9/2003 | Ogilvie et al. |
| 6,620,356 B1 | 9/2003 | Wong et al. |

(56) References Cited

U.S. PATENT DOCUMENTS

| | | |
|---|---|---|
| 6,641,613 B2 | 11/2003 | Sennett |
| 6,648,915 B2 | 11/2003 | Sazy |
| 6,652,533 B2 | 11/2003 | O'Neil |
| 6,669,710 B2 | 12/2003 | Moutafis et al. |
| 6,673,113 B2 | 1/2004 | Ralph et al. |
| 6,679,887 B2 | 1/2004 | Nicholson et al. |
| 6,695,882 B2 | 2/2004 | Bianchi et al. |
| 6,699,288 B2 | 3/2004 | Moret |
| 6,709,438 B2 | 3/2004 | Dixon et al. |
| 6,719,760 B2 | 4/2004 | Dorchak et al. |
| 6,719,795 B1 | 4/2004 | Cornwall et al. |
| 6,730,125 B1 | 5/2004 | Lin |
| 6,743,257 B2 | 6/2004 | Castro |
| 6,746,487 B2 | 6/2004 | Scifert et al. |
| 6,764,491 B2 | 7/2004 | Frey et al. |
| 6,773,437 B2 | 8/2004 | Ogilvie et al. |
| 6,800,093 B2 | 10/2004 | Nicholson et al. |
| 6,824,565 B2 | 11/2004 | Muhanna et al. |
| 6,830,574 B2 | 12/2004 | Heckele et al. |
| 6,852,126 B2 | 2/2005 | Ahlgren |
| 6,890,728 B2 | 5/2005 | Dolecek et al. |
| 6,899,712 B2 | 5/2005 | Moutafis et al. |
| 6,923,792 B2 | 8/2005 | Staid et al. |
| 6,929,646 B2 | 8/2005 | Gambale |
| 6,942,665 B2 | 9/2005 | Gambale |
| 6,960,182 B2 | 11/2005 | Moutafis et al. |
| 6,962,592 B2 | 11/2005 | Gatturna et al. |
| 6,969,523 B1 | 11/2005 | Mattern et al. |
| 6,974,480 B2 | 12/2005 | Messerli et al. |
| 6,991,653 B2 | 1/2006 | White et al. |
| 6,994,728 B2 | 2/2006 | Zubok et al. |
| 7,004,946 B2 | 2/2006 | Parker et al. |
| 7,008,431 B2 | 3/2006 | Simonson |
| 7,014,640 B2 | 3/2006 | Kemppainen et al. |
| 7,025,742 B2 | 4/2006 | Rubenstein et al. |
| 7,025,769 B1 | 4/2006 | Ferree |
| 7,033,317 B2 | 4/2006 | Pruitt |
| 7,041,136 B2 | 5/2006 | Goble et al. |
| 7,066,961 B2 | 6/2006 | Michelson |
| 7,077,864 B2 | 7/2006 | Byrd, III et al. |
| 7,094,257 B2 | 8/2006 | Mujwid et al. |
| 7,122,017 B2 | 10/2006 | Moutafis et al. |
| 7,128,760 B2 * | 10/2006 | Michelson ................ 623/17.15 |
| 7,135,043 B2 | 11/2006 | Nakahara et al. |
| 7,182,782 B2 | 2/2007 | Kirschman |
| 7,204,825 B2 | 4/2007 | Cimino et al. |
| 7,207,992 B2 | 4/2007 | Ritland |
| 7,211,112 B2 | 5/2007 | Baynham et al. |
| 7,214,186 B2 | 5/2007 | Ritland |
| 7,223,292 B2 | 5/2007 | Messerli et al. |
| 7,232,463 B2 | 6/2007 | Falahee |
| 7,238,203 B2 | 7/2007 | Bagga et al. |
| 7,255,703 B2 | 8/2007 | Mujwid et al. |
| 7,267,691 B2 | 9/2007 | Keller et al. |
| 7,273,498 B2 | 9/2007 | Bianchi et al. |
| 7,288,093 B2 | 10/2007 | Michelson |
| 7,316,070 B2 | 1/2008 | Green |
| 7,329,283 B2 | 2/2008 | Estes et al. |
| 7,337,538 B2 | 3/2008 | Moutafis et al. |
| 7,341,590 B2 | 3/2008 | Ferree |
| 7,341,591 B2 | 3/2008 | Grinberg |
| 7,357,284 B2 | 4/2008 | Jauvin |
| 7,357,804 B2 | 4/2008 | Binder, Jr. et al. |
| 7,361,178 B2 | 4/2008 | Hearn et al. |
| 7,364,657 B2 | 4/2008 | Mandrusov et al. |
| 7,371,239 B2 | 5/2008 | Dec et al. |
| 7,377,923 B2 | 5/2008 | Purcell et al. |
| 7,387,643 B2 | 6/2008 | Michelson |
| 7,399,041 B2 | 7/2008 | Prentner et al. |
| D574,495 S | 8/2008 | Petersen |
| 7,406,775 B2 | 8/2008 | Funk et al. |
| 7,410,334 B2 | 8/2008 | McGrew |
| 7,410,478 B2 | 8/2008 | Yang |
| 7,413,065 B2 | 8/2008 | Gauthier |
| 7,421,772 B2 | 9/2008 | Gao et al. |
| 7,429,270 B2 | 9/2008 | Baumgartner et al. |
| D579,562 S | 10/2008 | Anderson et al. |
| 7,430,945 B2 | 10/2008 | Gauthier et al. |
| 7,431,711 B2 | 10/2008 | Moutafis et al. |
| 7,442,208 B2 | 10/2008 | Mathieu et al. |
| 7,455,157 B2 | 11/2008 | Kimes et al. |
| D582,552 S | 12/2008 | Berberich |
| 7,461,803 B2 | 12/2008 | Boerner |
| 7,473,255 B2 | 1/2009 | McGarity et al. |
| 7,476,226 B2 | 1/2009 | Weikel et al. |
| 7,478,577 B1 | 1/2009 | Wheeler |
| 7,481,766 B2 | 1/2009 | Lee et al. |
| 7,481,813 B1 | 1/2009 | Purcell |
| 7,485,145 B2 | 2/2009 | Purcell |
| D589,626 S | 3/2009 | Petersen |
| 7,501,073 B2 | 3/2009 | Wen et al. |
| 7,503,933 B2 | 3/2009 | Michelson |
| 7,503,934 B2 | 3/2009 | Eisermann et al. |
| 7,503,936 B2 | 3/2009 | Trieu |
| D590,943 S | 4/2009 | Petersen |
| D590,945 S | 4/2009 | Berberich |
| 7,513,901 B2 | 4/2009 | Scifert et al. |
| D593,202 S | 5/2009 | Petersen |
| 7,531,003 B2 | 5/2009 | Reindel |
| 7,534,265 B1 | 5/2009 | Boyd |
| 7,534,270 B2 | 5/2009 | Ball |
| D594,119 S | 6/2009 | Berberich et al. |
| 7,553,320 B2 | 6/2009 | Molz, IV et al. |
| D597,669 S | 8/2009 | Petersen |
| D598,096 S | 8/2009 | Petersen |
| D599,015 S | 8/2009 | Petersen |
| 7,578,820 B2 | 8/2009 | Moore et al. |
| D600,806 S | 9/2009 | Horton et al. |
| D601,251 S | 9/2009 | Horton et al. |
| 7,582,058 B1 | 9/2009 | Miles et al. |
| 7,582,107 B2 | 9/2009 | Trail et al. |
| 7,595,043 B2 | 9/2009 | Hedrick et al. |
| D603,502 S | 11/2009 | Petersen |
| 7,615,078 B2 | 11/2009 | White et al. |
| 7,618,423 B1 | 11/2009 | Valentine et al. |
| 7,625,374 B2 | 12/2009 | Branch et al. |
| 7,632,276 B2 | 12/2009 | Fishbein |
| D608,001 S | 1/2010 | Reardon et al. |
| 7,655,027 B2 | 2/2010 | Michelson |
| 7,658,766 B2 | 2/2010 | Melkent et al. |
| 7,671,014 B2 | 3/2010 | Beals et al. |
| 7,674,297 B2 | 3/2010 | Falahee |
| 7,677,418 B2 | 3/2010 | Henniges et al. |
| 7,686,805 B2 | 3/2010 | Michelson |
| 7,691,133 B2 | 4/2010 | Partin et al. |
| 7,693,562 B2 | 4/2010 | Marino et al. |
| 7,699,852 B2 | 4/2010 | Frankel et al. |
| 7,708,761 B2 | 5/2010 | Petersen |
| 7,717,685 B2 | 5/2010 | Moutafis et al. |
| 7,722,530 B2 | 5/2010 | Davison |
| 7,722,613 B2 | 5/2010 | Sutterlin et al. |
| 7,723,291 B2 | 5/2010 | Beals et al. |
| 7,728,868 B2 | 6/2010 | Razzaque et al. |
| 7,730,563 B1 | 6/2010 | Sklar et al. |
| 7,734,327 B2 | 6/2010 | Colquhoun |
| 7,740,634 B2 | 6/2010 | Orbay et al. |
| 7,740,661 B2 | 6/2010 | Baratz et al. |
| 7,744,555 B2 | 6/2010 | DiMauro et al. |
| 7,744,637 B2 | 6/2010 | Johnson et al. |
| 7,744,973 B2 | 6/2010 | Schoenle et al. |
| D620,108 S | 7/2010 | Eitenmueller et al. |
| 7,749,231 B2 | 7/2010 | Bonvallet et al. |
| 7,749,253 B2 | 7/2010 | Zucherman et al. |
| 7,749,269 B2 | 7/2010 | Peterman et al. |
| 7,749,273 B2 | 7/2010 | Cauthen et al. |
| 7,749,274 B2 | 7/2010 | Razian |
| 7,749,276 B2 | 7/2010 | Fitz |
| 7,749,279 B2 | 7/2010 | Twomey et al. |
| 7,749,555 B2 | 7/2010 | Zanella |
| 7,751,865 B2 | 7/2010 | Jascob et al. |
| 7,753,911 B2 | 7/2010 | Ray et al. |
| 7,753,914 B2 | 7/2010 | Ruhling et al. |
| 7,753,938 B2 | 7/2010 | Aschmann et al. |
| 7,753,940 B2 | 7/2010 | Veldman et al. |

(56) References Cited

U.S. PATENT DOCUMENTS

| | | |
|---|---|---|
| 7,753,962 B2 | 7/2010 | Melder |
| 7,758,501 B2 | 7/2010 | Frasier et al. |
| 7,758,616 B2 | 7/2010 | LeHuec et al. |
| 7,758,617 B2 | 7/2010 | Iott et al. |
| 7,758,644 B2 | 7/2010 | Trieu |
| 7,758,648 B2 | 7/2010 | Castleman et al. |
| 7,763,025 B2 | 7/2010 | Assell et al. |
| 7,763,035 B2 | 7/2010 | Melkent et al. |
| 7,763,055 B2 | 7/2010 | Foley |
| 7,763,078 B2 | 7/2010 | Peterman et al. |
| 7,763,080 B2 | 7/2010 | Southworth |
| D621,509 S | 8/2010 | Lovell |
| D622,395 S | 8/2010 | Iott et al. |
| D622,843 S | 8/2010 | Horton |
| D622,851 S | 8/2010 | Horton |
| 7,766,914 B2 | 8/2010 | McCormack et al. |
| 7,766,918 B2 | 8/2010 | Allard et al. |
| 7,766,930 B2 | 8/2010 | DiPoto et al. |
| 7,766,940 B2 | 8/2010 | Kwak et al. |
| 7,766,967 B2 | 8/2010 | Francis |
| 7,766,969 B2 | 8/2010 | Justin et al. |
| 7,769,422 B2 | 8/2010 | DiSilvestro et al. |
| 7,771,143 B2 | 8/2010 | Bharadwaj et al. |
| 7,771,475 B2 | 8/2010 | Michelson |
| 7,771,476 B2 | 8/2010 | Justis et al. |
| 7,771,479 B2 | 8/2010 | Humphreys et al. |
| 7,776,040 B2 | 8/2010 | Markworth et al. |
| 7,776,046 B2 | 8/2010 | Boyd et al. |
| 7,776,047 B2 | 8/2010 | Fanger et al. |
| 7,776,049 B1 | 8/2010 | Curran et al. |
| 7,776,075 B2 | 8/2010 | Bruneau et al. |
| 7,776,090 B2 | 8/2010 | Winslow et al. |
| 7,776,091 B2 | 8/2010 | Mastrorio et al. |
| 7,776,094 B2 | 8/2010 | McKinley et al. |
| 7,776,095 B2 | 8/2010 | Peterman et al. |
| 7,776,594 B2 | 8/2010 | Bays et al. |
| 7,780,707 B2 | 8/2010 | Johnson et al. |
| 7,794,396 B2 | 9/2010 | Gattani et al. |
| 7,794,501 B2 | 9/2010 | Edie et al. |
| 7,799,034 B2 | 9/2010 | Johnson et al. |
| 7,799,036 B2 | 9/2010 | Davison et al. |
| 7,799,053 B2 | 9/2010 | Haid et al. |
| 7,799,054 B2 | 9/2010 | Kwak et al. |
| 7,799,055 B2 | 9/2010 | Lim |
| 7,799,056 B2 | 9/2010 | Sankaran |
| 7,799,076 B2 | 9/2010 | Sybert et al. |
| 7,799,078 B2 | 9/2010 | Embry et al. |
| 7,799,083 B2 | 9/2010 | Smith et al. |
| 7,806,901 B2 | 10/2010 | Stad et al. |
| 7,811,327 B2 | 10/2010 | Hansell et al. |
| 7,811,329 B2 | 10/2010 | Ankney et al. |
| 7,815,681 B2 | 10/2010 | Ferguson |
| 7,819,801 B2 | 10/2010 | Miles et al. |
| D627,460 S | 11/2010 | Horton |
| 7,824,328 B2 | 11/2010 | Gattani et al. |
| 7,824,332 B2 | 11/2010 | Fakhrai |
| 7,824,410 B2 | 11/2010 | Simonson |
| 7,824,703 B2 | 11/2010 | Scifert et al. |
| 7,828,804 B2 | 11/2010 | Li et al. |
| 7,828,845 B2 | 11/2010 | Estes et al. |
| 7,828,849 B2 | 11/2010 | Lim |
| 7,837,713 B2 | 11/2010 | Petersen |
| 7,837,732 B2 | 11/2010 | Zucherman et al. |
| D628,694 S | 12/2010 | Donnez |
| D629,896 S | 12/2010 | Horton |
| 7,846,210 B2 | 12/2010 | Perez-Cruet et al. |
| 7,850,733 B2 | 12/2010 | Baynham et al. |
| 7,850,735 B2 | 12/2010 | Eisermann et al. |
| 7,850,736 B2 | 12/2010 | Heinz et al. |
| D631,156 S | 1/2011 | Halder et al. |
| 7,867,277 B1 | 1/2011 | Tohmeh |
| 7,897,164 B2 | 3/2011 | Scifert |
| 7,897,564 B2 | 3/2011 | Beals et al. |
| 7,905,840 B2 | 3/2011 | Pimenta et al. |
| 7,918,891 B1 | 4/2011 | Curran et al. |
| 7,927,361 B2 | 4/2011 | Oliver et al. |
| D637,721 S | 5/2011 | Horton |
| 7,935,124 B2 | 5/2011 | Frey et al. |
| 7,938,857 B2 | 5/2011 | Garcia-Bengochea et al. |
| 7,939,092 B2 | 5/2011 | McKay et al. |
| 7,951,107 B2 | 5/2011 | Staid et al. |
| 7,964,208 B2 | 6/2011 | Spagnoli et al. |
| D641,872 S | 7/2011 | Solingen et al. |
| D641,873 S | 7/2011 | Solingen et al. |
| D641,874 S | 7/2011 | Solingen et al. |
| D642,268 S | 7/2011 | Qureshi |
| 7,985,256 B2 | 7/2011 | Grotz et al. |
| D643,921 S | 8/2011 | Davila |
| D647,202 S | 10/2011 | Scifert |
| 8,080,521 B2 | 12/2011 | Beals et al. |
| 8,088,163 B1 | 1/2012 | Kleiner |
| D655,414 S | 3/2012 | Cuschieri et al. |
| D656,610 S | 3/2012 | Kleiner |
| 8,148,326 B2 | 4/2012 | Beals et al. |
| D660,428 S | 5/2012 | Hohl |
| 8,198,238 B2 | 6/2012 | Beals et al. |
| 8,246,572 B2 | 8/2012 | Cantor et al. |
| D667,542 S | 9/2012 | Kleiner |
| 8,277,510 B2 | 10/2012 | Kleiner |
| 8,292,960 B2 | 10/2012 | Kleiner |
| 8,293,232 B2 | 10/2012 | Beals et al. |
| 8,366,748 B2 | 2/2013 | Kleiner |
| D692,133 S | 10/2013 | Steinwachs et al. |
| 2002/0049448 A1 | 4/2002 | Sand et al. |
| 2002/0058947 A1 | 5/2002 | Hochschuler et al. |
| 2003/0083748 A1 | 5/2003 | Lee et al. |
| 2003/0149482 A1 | 8/2003 | Michelson |
| 2003/0171812 A1 | 9/2003 | Grunberg et al. |
| 2003/0229358 A1 | 12/2003 | Errico et al. |
| 2004/0002713 A1 | 1/2004 | Olson et al. |
| 2004/0024466 A1 | 2/2004 | Heerklotz et al. |
| 2004/0073314 A1 | 4/2004 | White et al. |
| 2004/0087956 A1 | 5/2004 | Weikel et al. |
| 2004/0133217 A1 | 7/2004 | Watschke |
| 2004/0143330 A1 | 7/2004 | Sazy |
| 2004/0148027 A1 | 7/2004 | Errico et al. |
| 2004/0153158 A1 | 8/2004 | Errico et al. |
| 2004/0167532 A1 | 8/2004 | Olson, Jr. et al. |
| 2004/0176853 A1 | 9/2004 | Sennett et al. |
| 2004/0215201 A1 | 10/2004 | Lieberman |
| 2004/0230211 A1 | 11/2004 | Moutafis et al. |
| 2005/0112091 A1 | 5/2005 | DiMauro et al. |
| 2005/0124993 A1 | 6/2005 | Chappuis |
| 2005/0124994 A1 | 6/2005 | Berger et al. |
| 2005/0149035 A1 | 7/2005 | Pimenta et al. |
| 2005/0149192 A1 | 7/2005 | Zucherman et al. |
| 2005/0159765 A1 | 7/2005 | Moutafis et al. |
| 2005/0165405 A1 | 7/2005 | Tsou |
| 2005/0216002 A1 | 9/2005 | Simonson |
| 2005/0216018 A1 | 9/2005 | Sennett |
| 2005/0251257 A1 | 11/2005 | Mitchell et al. |
| 2005/0261781 A1 | 11/2005 | Sennett et al. |
| 2005/0283150 A1 | 12/2005 | Moutafis et al. |
| 2006/0004367 A1 | 1/2006 | Alamin et al. |
| 2006/0015184 A1* | 1/2006 | Winterbottom et al. ... 623/18.11 |
| 2006/0058807 A1 | 3/2006 | Landry et al. |
| 2006/0100304 A1 | 5/2006 | Vresilovic et al. |
| 2006/0111779 A1 | 5/2006 | Petersen |
| 2006/0111780 A1 | 5/2006 | Petersen |
| 2006/0116770 A1 | 6/2006 | White et al. |
| 2006/0122597 A1 | 6/2006 | Jones et al. |
| 2006/0154366 A1 | 7/2006 | Brown et al. |
| 2006/0155170 A1 | 7/2006 | Hanson et al. |
| 2006/0167461 A1 | 7/2006 | Hawkins et al. |
| 2006/0190081 A1 | 8/2006 | Kraus et al. |
| 2006/0229550 A1 | 10/2006 | Staid et al. |
| 2006/0247650 A1 | 11/2006 | Yerby et al. |
| 2006/0247791 A1 | 11/2006 | McKay et al. |
| 2006/0264808 A1 | 11/2006 | Staid et al. |
| 2006/0264964 A1 | 11/2006 | Scifert et al. |
| 2007/0003598 A1 | 1/2007 | Trieu |
| 2007/0043442 A1 | 2/2007 | Abernathie |
| 2007/0067034 A1 | 3/2007 | Chirico et al. |
| 2007/0073110 A1 | 3/2007 | Larson et al. |

(56) References Cited

U.S. PATENT DOCUMENTS

| | | |
|---|---|---|
| 2007/0073294 A1 | 3/2007 | Chin et al. |
| 2007/0088007 A1 | 4/2007 | Ng |
| 2007/0093850 A1 | 4/2007 | Harris et al. |
| 2007/0123985 A1 | 5/2007 | Errico et al. |
| 2007/0172790 A1 | 7/2007 | Doucette, Jr. et al. |
| 2007/0185496 A1 | 8/2007 | Beckman et al. |
| 2007/0208423 A1 | 9/2007 | Messerli et al. |
| 2007/0213596 A1 | 9/2007 | Hamada |
| 2007/0213717 A1 | 9/2007 | Trieu |
| 2007/0213718 A1 | 9/2007 | Trieu |
| 2007/0213822 A1 | 9/2007 | Trieu |
| 2007/0213826 A1 | 9/2007 | Smith et al. |
| 2007/0225219 A1 | 9/2007 | Boden et al. |
| 2007/0225811 A1 | 9/2007 | Scifert et al. |
| 2007/0242869 A1 | 10/2007 | Luo et al. |
| 2007/0250166 A1 | 10/2007 | McKay |
| 2007/0264300 A1 | 11/2007 | Scifert et al. |
| 2007/0265632 A1 | 11/2007 | Scifert et al. |
| 2007/0270951 A1 | 11/2007 | Davis et al. |
| 2007/0276406 A1 | 11/2007 | Mahoney et al. |
| 2007/0288007 A1 | 12/2007 | Burkus et al. |
| 2007/0293948 A1 | 12/2007 | Bagga et al. |
| 2008/0003255 A1 | 1/2008 | Kerr et al. |
| 2008/0009929 A1 | 1/2008 | Harris et al. |
| 2008/0033440 A1 | 2/2008 | Moskowitz et al. |
| 2008/0058606 A1 | 3/2008 | Miles et al. |
| 2008/0071284 A1 | 3/2008 | Lechmann et al. |
| 2008/0086142 A1 | 4/2008 | Kohm et al. |
| 2008/0125856 A1 | 5/2008 | Perez-Cruet et al. |
| 2008/0147191 A1 | 6/2008 | Lopez et al. |
| 2008/0154375 A1 | 6/2008 | Serhan et al. |
| 2008/0154377 A1 | 6/2008 | Voellmicke |
| 2008/0154381 A1 | 6/2008 | Parrish |
| 2008/0172127 A1 | 7/2008 | Perez-Cruet et al. |
| 2008/0195058 A1 | 8/2008 | Moutafis et al. |
| 2008/0243126 A1 | 10/2008 | Gutierrez et al. |
| 2008/0249569 A1 | 10/2008 | Waugh et al. |
| 2008/0255564 A1 | 10/2008 | Michelson |
| 2008/0260598 A1 | 10/2008 | Scifert et al. |
| 2008/0269904 A1 | 10/2008 | Voorhies |
| 2008/0288071 A1 | 11/2008 | Biyani et al. |
| 2008/0300598 A1 | 12/2008 | Barreiro et al. |
| 2009/0043312 A1 | 2/2009 | Koulisis |
| 2009/0076440 A1 | 3/2009 | Moutafis et al. |
| 2009/0076556 A1 | 3/2009 | McGarity et al. |
| 2009/0088765 A1 | 4/2009 | Butler et al. |
| 2009/0098184 A1 | 4/2009 | Govil et al. |
| 2009/0099660 A1 | 4/2009 | Scifert et al. |
| 2009/0105718 A1 | 4/2009 | Zhang et al. |
| 2009/0124860 A1 | 5/2009 | Miles et al. |
| 2009/0124980 A1 | 5/2009 | Chen |
| 2009/0125066 A1 | 5/2009 | Kraus et al. |
| 2009/0142385 A1 | 6/2009 | Gross et al. |
| 2009/0187194 A1 | 7/2009 | Hamada |
| 2009/0192350 A1 | 7/2009 | Mejia |
| 2009/0192403 A1 | 7/2009 | Gharib et al. |
| 2009/0198241 A1 | 8/2009 | Phan |
| 2009/0198245 A1 | 8/2009 | Phan |
| 2009/0198337 A1 | 8/2009 | Phan |
| 2009/0198338 A1 | 8/2009 | Phan |
| 2009/0198339 A1 | 8/2009 | Kleiner et al. |
| 2009/0203967 A1 | 8/2009 | Branch et al. |
| 2009/0204148 A1 | 8/2009 | Lenke |
| 2009/0204159 A1 | 8/2009 | Justis et al. |
| 2009/0204220 A1 | 8/2009 | Trieu |
| 2009/0222011 A1 | 9/2009 | Lehuec et al. |
| 2009/0228107 A1 | 9/2009 | Michelson |
| 2009/0246244 A1 | 10/2009 | McKay et al. |
| 2009/0248163 A1 | 10/2009 | King et al. |
| 2009/0259108 A1 | 10/2009 | Miles et al. |
| 2009/0264892 A1 | 10/2009 | Beyar et al. |
| 2009/0275995 A1 | 11/2009 | Truckai |
| 2009/0299477 A1 | 12/2009 | Clayton et al. |
| 2009/0306692 A1 | 12/2009 | Barrington et al. |
| 2010/0004752 A1 | 1/2010 | White et al. |
| 2010/0010367 A1 | 1/2010 | Foley et al. |
| 2010/0010524 A1 | 1/2010 | Barrington et al. |
| 2010/0016903 A1 | 1/2010 | Matityahu et al. |
| 2010/0016972 A1 | 1/2010 | Jansen et al. |
| 2010/0016973 A1 | 1/2010 | de Villiers et al. |
| 2010/0021518 A1 | 1/2010 | Scifert et al. |
| 2010/0030065 A1 | 2/2010 | Farr et al. |
| 2010/0036226 A9 | 2/2010 | Marino et al. |
| 2010/0036442 A1 | 2/2010 | Lauryssen et al. |
| 2010/0042221 A1 | 2/2010 | Boyd |
| 2010/0057208 A1 | 3/2010 | Dryer |
| 2010/0063516 A1 | 3/2010 | Parmer et al. |
| 2010/0063554 A1 | 3/2010 | Branch et al. |
| 2010/0076335 A1 | 3/2010 | Gharib et al. |
| 2010/0076445 A1 | 3/2010 | Pagano |
| 2010/0076446 A1 | 3/2010 | Gorek |
| 2010/0082036 A1 | 4/2010 | Reiley et al. |
| 2010/0087828 A1 | 4/2010 | Krueger et al. |
| 2010/0087875 A1 | 4/2010 | McGahan et al. |
| 2010/0100141 A1 | 4/2010 | de Villiers et al. |
| 2010/0105986 A1 | 4/2010 | Miles et al. |
| 2010/0105987 A1 | 4/2010 | Miles et al. |
| 2010/0112029 A1 | 5/2010 | Scifert |
| 2010/0121365 A1 | 5/2010 | O'Sullivan et al. |
| 2010/0121453 A1 | 5/2010 | Peterman |
| 2010/0125333 A1 | 5/2010 | Zdeblick et al. |
| 2010/0125338 A1 | 5/2010 | Fitz |
| 2010/0131020 A1 | 5/2010 | Heinz et al. |
| 2010/0137690 A1 | 6/2010 | Miles et al. |
| 2010/0137923 A1 | 6/2010 | Greenhalgh et al. |
| 2010/0145390 A1 | 6/2010 | McCarthy et al. |
| 2010/0145452 A1 | 6/2010 | Blaylock et al. |
| 2010/0145461 A1 | 6/2010 | Landry et al. |
| 2010/0160923 A1 | 6/2010 | Sand et al. |
| 2010/0160982 A1 | 6/2010 | Justis et al. |
| 2010/0161062 A1 | 6/2010 | Foley et al. |
| 2010/0161074 A1 | 6/2010 | McKay |
| 2010/0168755 A1 | 7/2010 | Reiley et al. |
| 2010/0168862 A1 | 7/2010 | Edie et al. |
| 2010/0174326 A1 | 7/2010 | Selover et al. |
| 2010/0185286 A1 | 7/2010 | Allard |
| 2010/0185287 A1 | 7/2010 | Allard |
| 2010/0185288 A1 | 7/2010 | Carls |
| 2010/0191334 A1 | 7/2010 | Keller |
| 2010/0191337 A1 | 7/2010 | Zamani et al. |
| 2010/0198140 A1 | 8/2010 | Lawson |
| 2010/0199483 A1 | 8/2010 | Justis et al. |
| 2010/0204798 A1 | 8/2010 | Gerbec et al. |
| 2010/0217398 A1 | 8/2010 | Keller |
| 2010/0222784 A1 | 9/2010 | Schwab et al. |
| 2010/0222824 A1 | 9/2010 | Simonson |
| 2010/0228294 A1 | 9/2010 | LeHuec et al. |
| 2010/0228351 A1 | 9/2010 | Ankney et al. |
| 2010/0234848 A1 | 9/2010 | Sutterlin et al. |
| 2010/0234957 A1 | 9/2010 | Zdeblick et al. |
| 2010/0249934 A1 | 9/2010 | Melkent |
| 2010/0256767 A1 | 10/2010 | Melkent |
| 2010/0256768 A1 | 10/2010 | Lim et al. |
| 2010/0262241 A1 | 10/2010 | Eisermann et al. |
| 2010/0262245 A1 | 10/2010 | Alfaro et al. |
| 2010/0266689 A1 | 10/2010 | Simonton et al. |
| 2010/0280622 A1 | 11/2010 | McKinley |
| 2010/0286778 A1 | 11/2010 | Eisermann et al. |
| 2010/0286784 A1 | 11/2010 | Curran et al. |
| 2010/0298938 A1 | 11/2010 | Humphreys et al. |
| 2010/0305575 A1 | 12/2010 | Wilkinson et al. |
| 2010/0312103 A1 | 12/2010 | Gorek et al. |
| 2010/0312290 A1 | 12/2010 | McKinley et al. |
| 2010/0312347 A1 | 12/2010 | Arramon et al. |
| 2010/0331847 A1 | 12/2010 | Wilkinson et al. |
| 2011/0014587 A1 | 1/2011 | Spagnoli et al. |
| 2011/0015748 A1 | 1/2011 | Molz, IV et al. |
| 2011/0020768 A1 | 1/2011 | Spagnoli et al. |
| 2011/0021427 A1 | 1/2011 | Amsden et al. |
| 2011/0028393 A1 | 2/2011 | Vickers et al. |
| 2011/0071536 A1 | 3/2011 | Kleiner |
| 2011/0093005 A1 | 4/2011 | Strokosz et al. |
| 2011/0106162 A1 | 5/2011 | Ballard et al. |
| 2011/0144755 A1 | 6/2011 | Baynham et al. |

(56) References Cited

U.S. PATENT DOCUMENTS

| | | | |
|---|---|---|---|
| 2011/0160777 | A1 | 6/2011 | Spagnoli et al. |
| 2011/0184412 | A1 | 7/2011 | Scifert et al. |
| 2011/0230970 | A1 | 9/2011 | Lynn et al. |
| 2012/0022651 | A1 | 1/2012 | Akyuz et al. |
| 2012/0035668 | A1 | 2/2012 | Manninen et al. |
| 2012/0065613 | A1 | 3/2012 | Pepper et al. |
| 2012/0065687 | A1 | 3/2012 | Ballard et al. |
| 2012/0078315 | A1 | 3/2012 | Sweeney |
| 2012/0136442 | A1 | 5/2012 | Kleiner |
| 2012/0259335 | A1 | 10/2012 | Scifert et al. |
| 2013/0073041 | A1 | 3/2013 | Scifert et al. |
| 2013/0110169 | A1 | 5/2013 | Hynes et al. |

OTHER PUBLICATIONS

U.S. Appl. No. 29/427,387, filed Jul. 17, 2012, Kleiner.
U.S. Appl. No. 29/433,403, filed Sep. 28, 2012, Kleiner.
U.S. Appl. No. 13/632,956, filed Oct. 1, 2012, Kleiner.
U.S. Appl. No. 13/714,971, filed Dec. 14, 2012, Kleiner.
Ray, C., "Facet Joint Disorders and Back Pain," published on Spine-Health, Dec. 10, 2002, available at www.spine-health.com/conditions/arthritis/facet-joint-disorders-and-back-pain, 1 page.
Staehler, R., "Spine Surgery for a Cervical Herniated Disc," published on Spine-Health, Jun. 12, 2002, available at www.spine-health.com/conditions/herniated-disc/spine-surgery-a-cervical-herniated-disc, 2 pages.
Staehler, R., "Summary of Cervical Herniated Disc Treatment Options," published on Spine-Health, Jun. 12, 2002, available at www.spine-health.com/conditions/herniated-disc/summary-cervical-herniated-disc-treatment-options, 1 page.
Ullrich, P.F., "Anterior Cervical Spinal Fusion Surgery," published on Spine-Health, Oct. 7, 2005, available at www.spine-health.com/treatment/back-surgery/anterior-cervical-spinal-fusion-surgery, 2 pages.
Ullrich, P.F., "Cervical Spinal Instrumentation," published on Spine-Health, Oct. 7, 2005, available at www.spine-health.com/treatment/back-surgery/cervical-spinal-instrumentation, 2 pages.
Wascher, T.M., "Anterior cervical decompression and spine fusion procedure," published on Spine-Health, Aug. 29, 2001, available at www.spine-health.com/treatment/spinal-fusion/anterior-cervical-decompression-and-spine-fusion-procedure, 2 pages.
"BAK® /Proximity™ (BP®) Cage", Zimmer Website, as early as Oct. 23, 2007, available at http://www.zimmer.com/z/ctl/op/global/action/1/id/7930/template/MP/prcat/M6/prod/y, printed on Jun. 8, 2009, 1 page.
"BAK® Vista® Radiolucent Interbody Fusion System", Zimmer Website, as early as Oct. 25, 2005, available at http://www.zimmerindia.com/z/ctl/op/global/action/1/id/7809/template/MP/prcat/M6/prod/y, printed on Jun. 8, 2009, pp. 1-2.
"Facet Joint Syndrome," The Cleveland Clinic Foundation, copyright 1995-2008, printed Nov. 19, 2008, available at http://my.clevelandclinic.org/disorders/facet_joint_syndrome/hic_facet_joint_syndrome.aspx, 2 pages.
"Screws, Cages or Both", Spine Universe Website, as early as Aug. 18, 2002, available at http://www.spineuniverse.com/displayarticle.php/article1363.html, printed on Jun. 8, 2009, pp. 1-13.
"University of Maryland Spine Program: A Patient's Guide to Anterior Lumbar Interbody Fusion with Intervertebral Cages", University of Maryland Medical Center website, as early as 2003, available at http://www.umm.edu/spinecenter/education/anterior_lumbar_interbody_fusion_with_intervertebral_cages.htm, printed on Jun. 8, 2009, pp. 1-4.
"Vertebral column," from Wikipedia, the free encyclopedia, printed May 19, 2009, retrieved from http://en.wikipedia.org/wiki/Vertebral_column, 6 pages.
"Zygapophysial joint," from Wikipedia, the free encyclopedia, printed May 19, 2009, retrieved from http://en.wikipedia.org/wiki/Zygapophysial_joint, 2 pages.
International Search Report for International (PCT) Patent Application No. PCT/US2009/033488, mailed. Mar. 25, 2009, 2 pages.
Written Opinion for International (PCT) Patent Application No. PCT/US2009/033488, mailed. Mar. 25, 2009, 9 pages.
Official Action for U.S. Appl. No. 12/632,720, mailed Jun. 7, 2012, 5 pages.
Official Action for U.S. Appl. No. 12/632,720, mailed Aug. 28, 2012, 5 pages.
Notice of Allowance for U.S. Appl. No. 12/632,720, mailed Oct. 5, 2012. 7 pages.
U.S. Appl. No. 29/453,829, filed May 3, 2013, Kleiner.
U.S. Appl. No. 13/947,255, filed Jul. 22, 2013, Kleiner.
Ehrenberg, "The 3-D Printing Revolution," Science News, Mar. 9, 2013, pp. 20-25.
U.S. Appl. No. 14/088,148, filed Nov. 22, 2013, Kleiner et al.

* cited by examiner

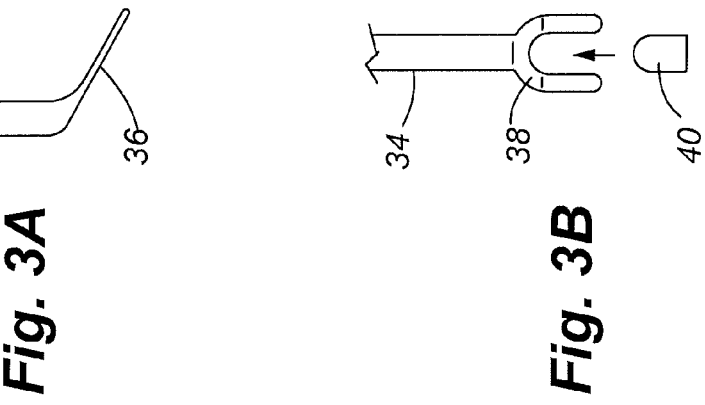
Fig. 3A
Fig. 3B
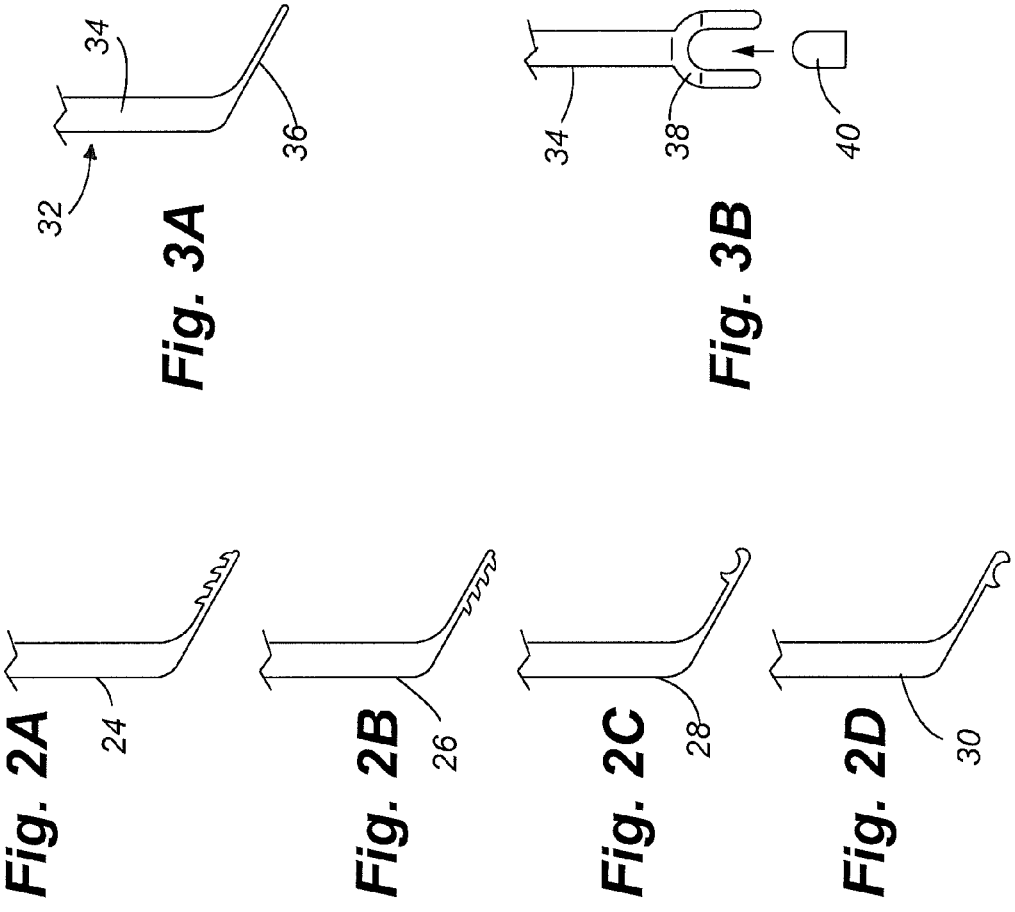
Fig. 2A
Fig. 2B
Fig. 2C
Fig. 2D
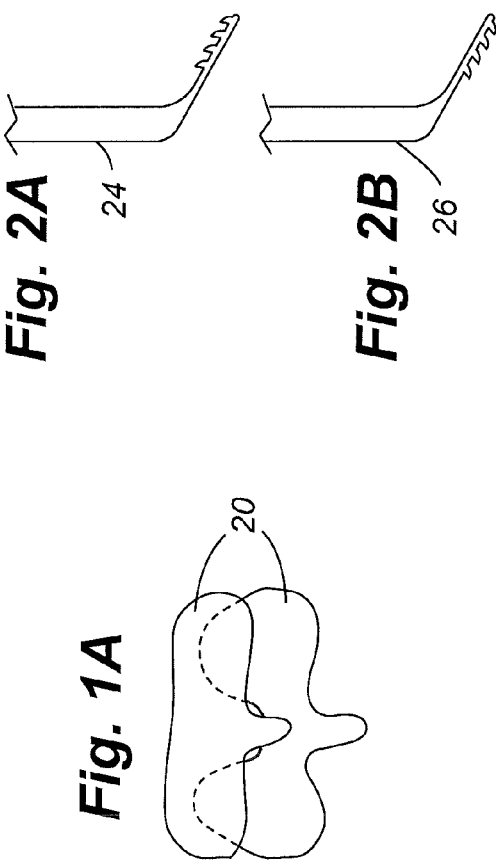
Fig. 1A
Fig. 1B Fig. 4A
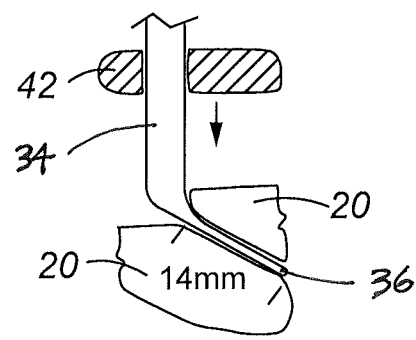
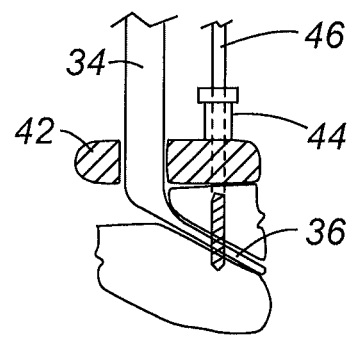
Fig. 4B

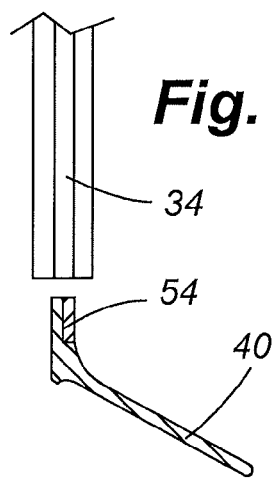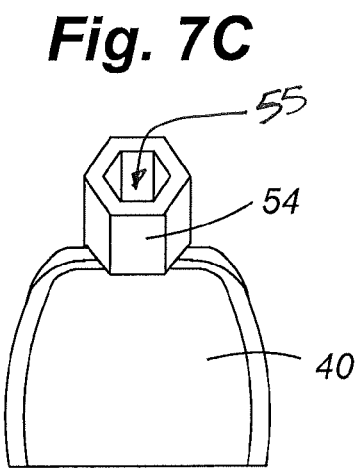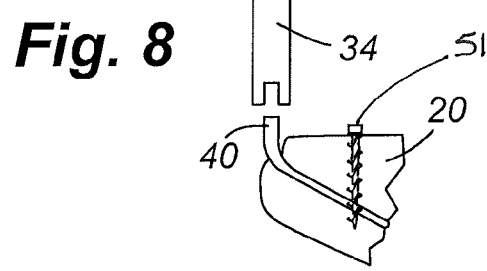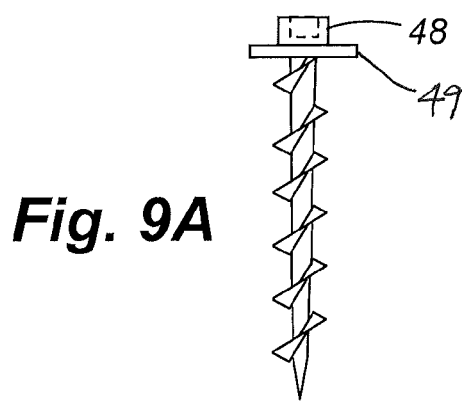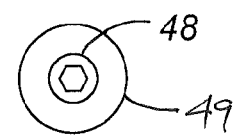

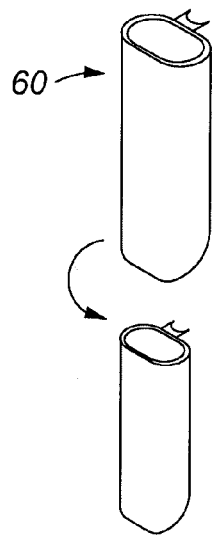
*Fig. 11A*
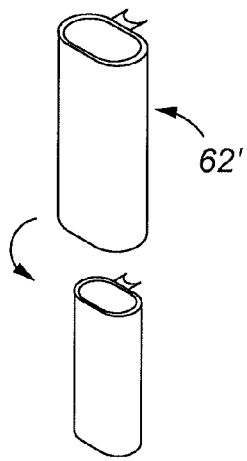
*Fig. 11B*
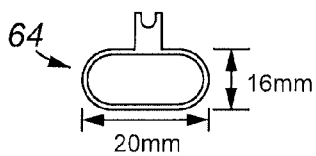
*Fig. 11C*
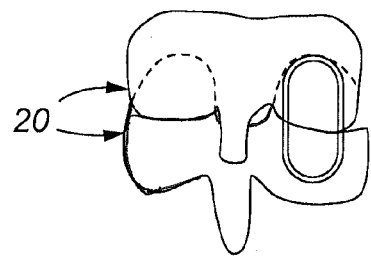
*Fig. 11D*
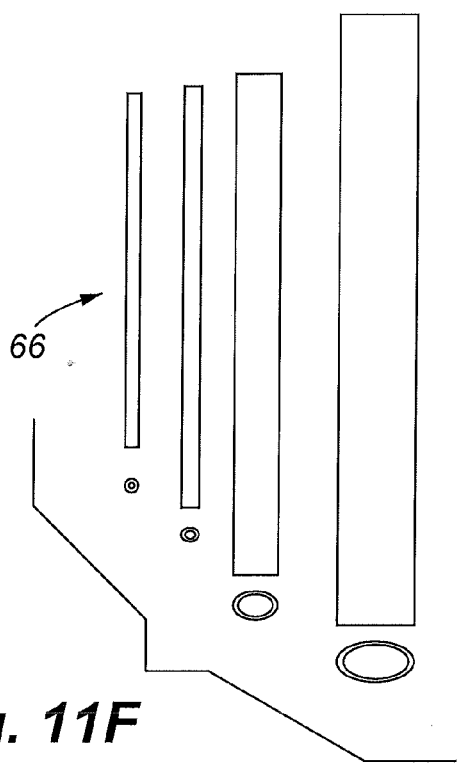
*Fig. 11F*
*Fig. 11E*

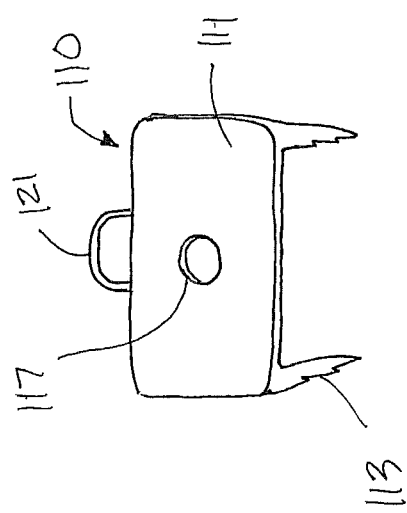
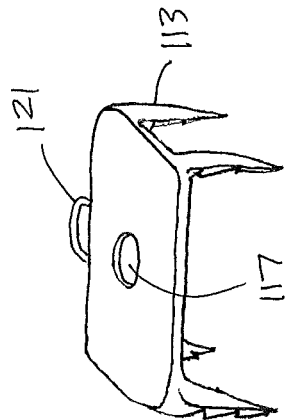
Fig. 14A
Fig. 14B

APPARATUS AND METHOD OF SPINAL IMPLANT AND FUSION

CROSS REFERENCE TO RELATED APPLICATIONS

This application is a continuation of U.S. patent application Ser. No. 12/632,720, filed on Dec. 7, 2009, which in turn claims priority to U.S. Provisional Patent Application No. 61/120,260, filed on Dec. 5, 2008, and U.S. Provisional Patent Application No. 61/186,683, filed on Jun. 12, 2009, the entire disclosures of which are incorporated by reference herein in their entireties.

FIELD OF THE INVENTION

This disclosure relates to orthopedic surgery, and more specifically to apparatus and methods for placing an implant into a patient, for example, to promote an intervertebral fusion.

BACKGROUND OF THE INVENTION

Individuals who suffer degenerative disc disease, natural spine deformations, a herniated disc, spine injuries or other spine disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. The surgical procedure will vary depending on the nature and extent of the injury.

For patients with varying degrees of degenerative disc disease and/or nerve compression with associated lower back pain, spinal fusion surgery, or lumbar arthrodesis ("fusion") is an effective method and commonly used to treat the degenerative disease. Fusion commonly involves distracting and/or decompressing one or more intervertebral spaces, followed by removing any associated facet joints or discs, and then joining or "fusing" two or more adjacent vertebra together. This fusion typically occurs with the assistance of an autographed or allographed bone graft. In certain operations, the fusion may also be assisted by a particular spinal implant or one or more bioactive materials.

Fusion of vertebral bodies involves fixation of two or more adjacent vertebrae. This procedure may be performed through introduction of rods or plates, and screws or other devices into a vertebral joint to join various portions of a vertebra to a corresponding portion on an adjacent vertebra. Fusion may occur in the lumbar, interbody or cervical spine region of a patient. A fusion is designed to stop and/or eliminate all motion in the spinal segment by destruction of some or all of the joints in that segment, and further utilizing bone graft material and/or rigid implantable fixation devices for securing the adjacent vertebrae. By eliminating movement, back pain and further degenerative disc disease may be reduced or avoided. Fusion requires tools for accessing the vertebrae and implanting the desired implant, bioactive material, etc. Such procedures often require introduction of additional tools to prepare a site for implantation. These tools may include drills, drill guides, debridement tools, irrigation devices, vises, clamps, cannulae, and other insertion/retraction tools.

Generally, there are five main types of lumbar fusion, including: posterior lumbar fusion ("PLF"), posterior lumbar interbody fusion ("PLIF"), anterior lumbar interbody fusion ("ALIF"), circumferential 360 fusion, and transforaminal lumbar interbody fusion ("TLIF"). A posterior approach is one that accesses the surgical site from the patient's back, and an anterior approach is one that accesses the surgical site from the patient's front or chest. There are similar approaches for fusion in the interbody or cervical spine regions.

Certain procedures are designed to achieve fixation of vertebral bodies, for example, in the cervical spine region, through a midline posterior approach. The main risk of the posterior approach is to the neural elements themselves. These include the nerve roots that are exiting the spinal canal as well as the central grouping of nerve roots called the cauda equine. The implants used in many of these procedures are bulky, over-engineered, or simply not designed for implant in the cervical spine, and therefore increased risk to the neural elements may occur while accessing and during implantation of the device. Should the implant become dislodged, move, or migrate, then those structures are again at risk. Such an approach also is time consuming and increases the hospital stay for the patient. Other risks include insertion and manipulation of the various apparatus required for minimally invasive surgery in this approach, including cannula, curettes, inserters, retractors, etc.

Alternatively, an anterior approach may be used to dissect the damaged joint and implant a fixation device. Many anterior approaches involve wiring the vertebral bodies together. However, anterior approaches are difficult when the patient is a heavy smoker or has hypothyroidism, and the chance of successful fusion decreases as a result.

Other disadvantages of traditional methods of spinal fusion include, for example, the pain associated with the procedure, the length of the procedure, the complexity of implements used to carry out the procedure, the prolonged hospitalization required to manage pain, the risk of infection due to the invasive nature of the procedure, and the possible requirement of a second procedure to remove the implantation device. These and other disadvantages are addressed by the present disclosure in more detail in the Summary and Detailed Description of the Preferred Embodiments, and the appended Claims.

SUMMARY OF THE INVENTION

One aspect of certain embodiments of the present disclosure relates to providing a minimally invasive method and apparatus for an implant to be placed in the joint space in an intervertebral joint after the removal of damaged joint tissue, and near simultaneous fixation of adjacent vertebral bodies. Certain embodiments relate to a minimally invasive method and apparatus for implanting an implant between one or more vertebral bodies, and more particularly in the cervical spine region.

Incorporated by reference in their entireties are the following U.S. patents and patent applications directed generally to methods and apparatus related to spinal procedures, thus providing written description support for various aspects of the present disclosure. The U.S. patents and pending applications incorporated by reference are as follows: U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865, 846 to Bryan, et al.; U.S. Pat. No. 5,569,246 to Ojima, et al.; U.S. Pat. No. 5,527,312 to Ray; and 2008/0255564 to Michelson.

In one embodiment of the present disclosure, an improved apparatus and method of providing fixation of adjacent vertebral bodies is provided by use of a device which comprises a handle, an elongated shaft, and a head that selectively grasps, for example, a bioactive material which is adapted to be inserted into the joint space at an intervertebral joint. In one embodiment of the present disclosure, the device can be placed in communication with a drill guide to direct a drill to the joint region, upon which a drill is used to create a hole in, for example, the facet joint. A facet screw may then be assembled into the hole. A specially designed screw both provides fixation for the vertebrae, and also helps to retain the implant material within the facet joint. According to other embodiments described herein, the screw may be omitted, or alternatively replaced with a staple or other fastening device.

In one embodiment of the present disclosure, a method of posterior spinal fixation includes using a device under microscopic control or loupe magnification to burr off the bottom of the facet joint. Curettes and rasps are used to prepare the facet joint to a bleeding surface. Then the head of the apparatus, preferably comprising a forked end attached to a flexible distal shaft, is fitted with bioactive material, and is placed between the leaves of the joint. A drill guide is then lowered over the shaft of the apparatus until it is adjacent to the facet joint. The drill is used to create hole(s) through the facet joint. A specially designed screw or other fastening device is then assembled through the hole(s) or otherwise adjacent the facet, thereby trapping the bioactive material in the joint. The apparatus is then removed, leaving the bioactive material in the joint space. This method is accomplished in a minimally invasive manner to provide near-simultaneous fixation of the vertebral bodies surrounding the facet joint.

According to this embodiment of the present disclosure, the apparatus is provided with a head that has one or more tines creating a "fork" shaped end, and the head being in communication with a flexible shaft. The head can be prefitted with an implantable material, for example, a bioactive material in such a manner so that the material can be easily manipulated into the facet joint. The forked end may have a mechanism that enables it to release the material once a facet screw has secured the material in the joint. The apparatus may be constructed so that the forked end can be manipulated, by way of the flexible shaft, in at least one dimension relative to the shaft. The apparatus may further be constructed to permit the forked end to comprise a first orientation, wherein the bioactive material is retained by the head of the apparatus, and a second orientation, wherein the bioactive material is released from the head of the apparatus. According to this embodiment, the surgeon may selectively retain or release the bioactive material by operation of the apparatus.

The head of the apparatus can be any of a plurality of shapes, for example, an arcuate shaped head, where the head is asymmetrically secured to the distal shaft. Also by way of example but not limitation, a head may be comprised of a variably rigid material. The variably rigid material may be designed to allow the bioactive material to be, for example, frictionally or mechanically held in place, and released upon application of a particular force. In another embodiment of the apparatus, the head may be made of a semi-flexible material that is capable of grasping the bioactive material and releasing the bioactive material when a particular force is applied, for example, a force in a particular dimension, or, for example, once a particular torque is transmitted from the shaft to the head of the apparatus.

Yet another aspect of the present disclosure is that the head itself is comprised of the implant material. Thus, for example, the head may be selectively attached to the shaft of the apparatus, and thereafter, selectively detached from the shaft of the material once the head is placed in the implant site. According to this embodiment, the head is part of the implant and remains in the patient with the implant material. One having skill in the art will appreciate that the head may be selectively attached to the shaft, for example, by means that mechanically grasp the head, means that attach by vacuum, means that attach by friction, and means that attach by magnetism, or other means known to those of skill in the art for attaching the head of an apparatus to the shaft of an apparatus.

In another embodiment of the design, the graft material is prefabricated and combined with a semi-rigid material. This composite has a hexagonal end that fits into the metal handle of the drill guide section, which allows introduction of the material into the joint and simple detachment of the grafting material from the introduction tool. The hexagonal end has a built-in angle corresponding to the angle of the facet joint. Accordingly, the angle is approximately 45 degrees in the cervical spine, the angle is approximately 90 degrees in the thoracic spine, and the angle is approximately 180 degrees in the lumbar spine.

The prefabricated complex of osteobiologic material insertion handle is a unique combination that allows for ease of insertion and maximizes the grafting surface area. The handle portion can be an inert non-absorbable material including, for example, nylon or slowly absorbing poly gel acetate, either of which have the attachment of biomaterial incorporated. The extra-articular section of the composite can be trimmed at the joint surface once the joint has been stabilized by the screw, which further secures the grafting material in place.

According to one embodiment of the present disclosure, the head may be selected from one or more bioactive materials, such that the head is the implant. This bioactive implant may further comprise an absorbable band, which preferably attaches to the shaft via a resorbable hex-shaped connection. According to alternate embodiments, the head may further comprise multiple absorbable bands which assist in attaching the head to the shaft. This configuration provides an implant that is distinguishable from other spinal implants, which are made exclusively of a single type of material (e.g., bone, autographed bone, graphed, allograft bone graft, etc.) According to yet an another alternate embodiment, the bioactive implant material comprising one or more absorbable bands which attaches to the shaft via a resorbable hex-shaped connector may be provided with a instrument head that does not remain in the patient with the implant material.

Yet another aspect of the present disclosure relates to the provision of a distal end of a shaft of the apparatus that is flexible to allow, for example, the user to maneuver the head and material to the implantation site. One skilled in the art will appreciate that the flexible aspect of certain embodiments can be both passive and active in nature. Active flexibility and manipulation in the distal end of the shaft may incorporate, for example, the manipulative capabilities of an endoscope, including components for manipulation such as guidewires along the longitudinal axis of the shaft of the apparatus. U.S. Pat. No. 5,704,892 is incorporated by reference herein in its entirety for the purpose of demonstrating the manipulative capabilities of a surgical tool, such as the one contemplated by this disclosure.

It is another aspect of the present disclosure that the distal end of the shaft be equipped with various other tools to aid in the procedure. Such tools may include, for example, devices used to assess the condition of the implantation site and surrounding tissue. This may include, for example, a device that transmits or provides an image or signal which carries an image for visual inspection and photography. Such an image capture device may include, for example, a device to illuminate the implant site coupled with an image capture and/or transmission device. Another tool may also include, for example, a device that aids in irrigation or drainage of the surgical site, a tool used to sample or biopsy tissue.

In another embodiment of the present disclosure, the head of the apparatus is angled and is shaped to allow ideal access and placement of the implant in the joint. For example, the angle and shape of the head relative to the shaft may be optimized for a particular implant site. The angle, for example, may be selectively variable or affixed. This angle may further depend on the specific vertebrae that form the implant site. Since the spinal column is a curved structure, angle requirements may differ with each implant site. The angle may also depend on which side of the vertebrae the implant is occurring.

Another factor may be whether the surgical approach to the joint is done from a superior or inferior approach. Yet another factor that may affect the shape and angle of the head is the age or physiology of the patient. Yet another factor is the angle of approach to the implant site through the muscle or other tissue. For example, according to various embodiments described in more detail herein, the use of angled cannula may permit a surgeon to access multiple levels of vertebrae through a single incision, in part by use of angled cannula to access facet joints adjacent the facet joint aligned with the incision. One skilled in the art will appreciate that as surgical techniques and methods develop, the apparatus may be adapted, for example, to offer different angles of introduction to an implant site to be manufactured into different shapes and from materials, and to provide access to other devices.

One skilled in the art will appreciate that the end of the apparatus need not be limited to a forked shape. The head may be of a forked shape, for example, that consists of one or more tines, or alternatively may be subs square or rectangular in shape. The head may also be, for example, retractable in nature. The apparatus may be, for example, capable of being operated in an arthroscopic procedure. Forms and designs that relate to the provision of an end of an apparatus to perform particular functions including, for example, grasping a material, selectively releasing a material, maneuvering, providing access for other devices, and providing other surgical, evaluative, exploratory, educational or investigatory functions are hereby incorporated into this disclosure.

In another aspect of an embodiment of the present disclosure, the shaft of the apparatus may be curved and/or may have an angular aspect. This shape in the shaft may, for example, aid the surgeon in more comfortably introducing the head of the apparatus to the implant site, be shaped to better accommodate implantation sites on right or left sides of the body, or be shaped to better accommodate right- or left-handed surgeons. The shaft of the apparatus may also be shaped to allow introduction of an implant to the portion of the spine which is traditionally accessed by posterior means. One having skill in the art will appreciate that the shaft of the apparatus may have multiple angles and curved aspects which enable aspects of embodiments of the present disclosure or aid in ergonomics.

One having skill in the art will appreciate that embodiments of the present disclosure may have various sizes. The sizes of the various elements of embodiments of the present disclosure may be sized based on various factors including, for example, the anatomy of the implant patient, the person or other device operating the apparatus, the implant location, physical features of the implant including, for example, with, length and thickness, and the size of the drill or other surgical tool being used with the apparatus.

In yet another embodiment of the present disclosure, the head is manufactured of a material and to dimensions that allow the head to serve as a spacer between the leaves of the joint at an implant site. The apparatus is then fitted with a device or other means to inject implant material into the joint space. This implant material may include, for example, a fast-curing epoxy or cement, a fast-curing bioactive cement, a cell culture, or other biologically inert substance. This injection may occur before, after, or during drilling and/or assembly of a screw into the joint space.

Alternatively, a screw is not required where the injected implant material sufficiently provides mechanical support to the joint. Once the implant material is injected into the joint space, the head and the apparatus may be removed from the implant site. Alternatively, the head may be selectively detached from the shaft of the apparatus and remain in the joint space to, for example, provide mechanical support, or serve to encase the injected implant material. One having skill in the art will appreciate the material and dimension requirements of the head and apparatus that will enable this embodiment.

The current disclosure is unique in that it integrates the process of facet joint fusion with near simultaneous fixation. Another unique feature is that the entire process can be performed using minimally invasive or endoscopic techniques. One of the features of the present disclosure is that it allows the majority of the joint to be prepared for fusion (as opposed to <10% of the joint with, for example, a TruFuse dowel). One embodiment of the present disclosure has a prefabricated piece of biomaterial shaped to fit into the regionally differently angled facet joints of the cervical, thoracic and/or lumbar facets. The bioactive membrane can be made of a variety of materials including, for example, demineralized bone matrix, a flexible collagenous polymer and a semi-solid putty or a viscoelastic matrix. This membrane can be introduced into the prepared facet joint, virtually filling it and resulting in an increase in the surface area for fusion.

According to certain embodiments, a drill may be used to create one or more hole(s) for inserting a screw, staple, or other fastening device for assisting in retaining the bioactive membrane material. A drill hole which traverses the facet joint and the bioactive material may also serve as a conduit through which semi-liquid or liquid materials can be directly placed in contact with the biomembrane. These combined materials can stimulate the bone formation process, for example, by adding substrate such a bone morphogenic protein, platelet rich plasma concentrate, or growth hormone, directly inoculating the joint-encased membrane. In a similar strategy, the painful small joints of the body can be so treated where amenable to fusion. One can use this strategy to fuse the interphalangeal joints of the fingers or toes by preparing the cartilage surface of the joint as describe above, and in the same endoscopic fashion applying the bioactive membrane. The drill hole can then be used to infiltrate the stimulating fusion concoction. In these types of applications a cancellous bone screw, or other fastening device may then be added through the drill hole(s) to stabilize the joint and lock the membrane in an ideal position.

The drill hole that traverses the implant site and bioactive material may further serve as a conduit for introducing one or more semi-liquid or liquid materials (including, for example, bone morphogenic substrates, bone marrow aspirate, plasma concentrate or other hormonal substance) which accelerate the fusion process. In addition, bioresorbable cements, which are currently in use for vertebroplasty procedures, could be installed through the drill hole portal to affect immediate joint stabilization. This novel approach to the application of additional bioative materials increases the utility of this approach because it allows an epoxy-like separation between the components of the fusion allowing placement of the bioactive membrane prior to the activation of the fusion process. The applied cancellous screw locks the bioactive membrane in place and stabilizes the respective joint.

Embodiments of the present disclosure are particularly suited for situations where anterior fixation or a rigid system is already in place in the anterior column of the spine. The literature reveals that a three level instrumented anterior cervical fusion will develop a pseudoarthrosis in at least one level up to 50% of the time. The use of supplemental posterior fixation increases the likelihood of the fusion succeeding >90% of the time but is fraught with substantial risks of bleeding and infection, not to mention the patient morbidity associated with the severe pain of posterior cervical exposures, the large foreign body burden (from rods and screws) the permanent muscle damage from soft tissue stripping and the expense of additional days in the hospital due solely to the exposure. If the posterior procedure can be performed with minimal invasion it would justify its use in the reduction of the pseudoarthrosis rate, costs of re-operation rates and patient suffering.

Another unique tool in this disclosure is a bioactive membrane which can be made of, by way of example but not limitation, demineralized bone, Hydroxyapatite sheet, a flexible Type I caliginous polymer, a viscoelastic matrix, and/or semi-solid putty which can be directly introduced into the joint. The prefabricated and pre-shaped bioactive membranes are specifically designed to fit into the implant site based upon the regional anatomical differences. This design allows for virtual filling of the joint with a resultant increase in the chance for fusion.

Another unique strategy afforded by this design is that the facet joint establishes a key to the anatomy of the vertebral body. Once the facet is located and the cannulae are inserted into the joint, reproducible access can be gained to the other associated vertebral structures. The spinous process, lamina, pedicle, neural foramen, medial spinal canal and lateral recess can all be reproducibly engaged once the facet joint relationship has been established. Attachment to this landmark allows navigation to other sites for robotic and radio navigation techniques.

Embodiments of the present disclosure present several advantages over the prior art including, for example, the speed of the procedure, the minimally invasive aspect of the procedure, the ability to introduce the implant material to the implant site with minimal risk and damage to the surrounding tissue, the lower risk of infection, more optimally placed vertebral implants, a more stable method of drilling and placing screws into an implant and fixation site in a near simultaneous fashion to reduce the likelihood of the implant material becoming dislodged prior to fixation, and fewer tools in a surgical site due to the integration of an implant placement tool with a drill guide.

Unlike other techniques describing facet joint fusion that employ a leap of faith technology, this process works reproducibly and is safe. In addition, unlike other devices, this process keys on the facet joint, a structure that is present from the cervical to the lumbosacral junction and is, therefore, amenable to treatment for facetogenic problems or for fusion from the C2 to S1 levels. Other techniques recognize their limitation and describe fixation of the lumbar or the cervical spine only, let alone simultaneous fusion and stabilization of the spine at all levels.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials.

One having skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

Another unique tool in the present disclosure is a cannula having a shape other than round (e.g., oval, pointed, square cornered, etc.) and having an end (e.g., the end inserted into the patient, distal from the user) that is angled and/or shaped to be ideally seated in a surgical site. Asymmetrical cannulas may allow visualization of the facet joint (DePuy has apparently described oval cannulas). An "egg-shaped" cross section may allow for the best view of the facet joint and minimizes the medial-lateral dissection that a round cannula would require.

Still other aspects of the invention are directed to cannula instruments that have a patient contacting end that is adjustable to assume a predetermined conformation. Thus, in one embodiment, material forms the tip end that comes into contact with bone, tissue, and particularly near especially nerve tissue, with such cannula end material being malleable to an extent necessary for the surgeon to mold the end conformation such that it achieves desired avoidance of particular structures encountered in any particular surgery. Thus, if a bony outcropping, a nerve fiber, etc. is perceived by the surgeon, the cannula tip end can be adjusted to avoid undesired contact or interference with such tissues or structures. In particular embodiments, the ability to adjust the geometric parameters of the tip end is achieved by manipulation of the other end of the instrument. For example, providing a turnable component at the opposite end of the instrument, the shape of the other end of the instrument (i.e. the end inserted into the patient) can be adjusted to either expand circumference, reduce circumference, render the opening more or less oblong, etc. In such a manner, it is possible to avoid having to remove the instrument or cannula from the patient's site to adjust the morphology of the instrument or cannula operating end, thus saving time, avoiding undesired reinsertion procedures, etc.

The present disclosure and the embodiments described herein have unique integration of fusion and stabilization using a minimally invasive approach. The technique further allows the preparation of the majority of facet joints in any area of the spine. Furthermore, the same process can be applied to other joints in the body and/or in veterinary applications for the spine and peripheral minor and major joints. One having skill in the art will appreciate that this can be achieved by placing the pre-formed biological material complex into the joint after the joint is prepared with the associated drill guide jig and then applying a screw across the joint as described above. Furthermore, and as described herein, several aspects of tools and methods of the present disclosure including, for example, the angle of the head, the drill bit, the screw type, the bioactive material and the cannula size, are dependent upon the particular anatomy of the patient, the joint and the implant site. A specific application of this technique would be to the interphalangeal joints of the fingers or toes to treat conditions of painful osteoarthritis.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 1A is a top elevation view of two adjacent cervical vertebrae;

FIG. 1B is a cross sectional view of a facet joint of the adjacent cervical vertebrae of FIG. 1A;

FIGS. 2A-2D are side elevation views of a variety of rasps and curettes that may be used to remove the cartilage and other tissue from between the vertebrae in the facet joint;

FIG. 3A is a side elevation view of an apparatus for providing an implantable material to the implantation site;

FIG. 3B is a front elevation view of the apparatus of FIG. 3A illustrating one example of how the implantable material is coupled to the head of the apparatus;

FIG. 4A is a side elevation view of the apparatus of FIG. 3A with a drill guide attached to the shaft of the apparatus;

FIG. 4B is a side elevation view of the apparatus of FIG. 3A where the drill guide is positioned above the drill site on the facet joint of FIG. 1B, and a drill has been placed in communication with the drill guide to create a hole through the facet joint;

FIG. 7B is the side elevation view of the assembly between the head of the apparatus and the partially hollow shaft of the apparatus shown in FIG. 7A;

FIG. 7C is a top elevation view of the partially hollow shaft and the head of the apparatus of FIG. 7B;

FIG. 8 is a side elevation view of a facet joint after a screw has been secured to the facet joint and the shaft of the apparatus has been removed from the head of the apparatus;

FIG. 9A is a side elevation view of a facet screw according to one embodiment of the present disclosure;

FIG. 9B is a top elevation view of a facet screw showing the head of a facet screw according to one embodiment of the present disclosure;

FIGS. 11A-11F are various views of a surgical cannula and dilators that are used in conjunction with certain embodiments of the present disclosure;

FIGS. 14A-14B are views of a lumbar spine fastening device according to one alternative embodiment of the present disclosure.

DETAILED DESCRIPTION

Figure 4C:
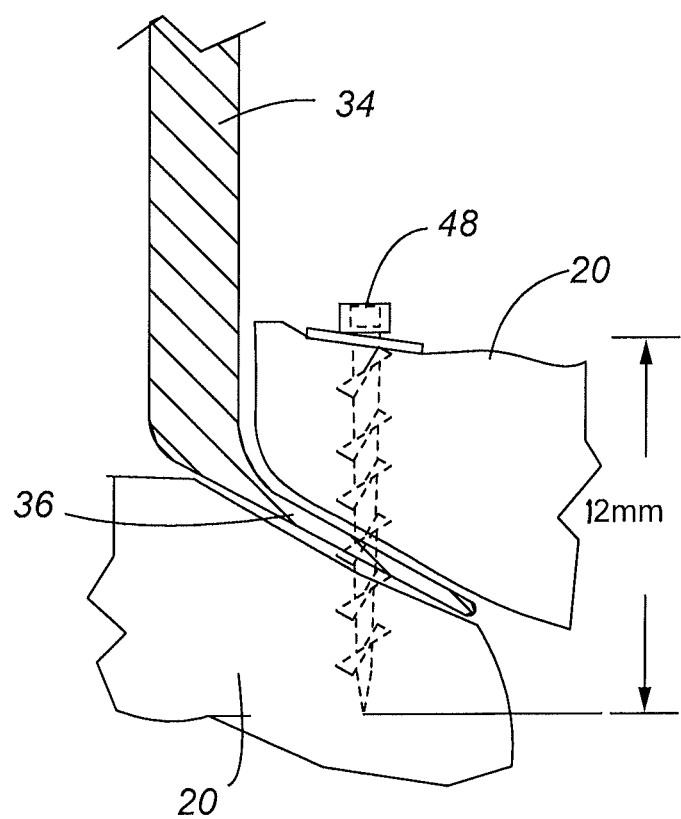
FIG. 4C is a detailed side elevation view of the facet joint of FIG. 1B after a screw has been secured to the facet joint.

According to various embodiments described herein, the present disclosure relates to an apparatus with a handle and a forked head on the distal end of the handle, which may be used to grasp bioactive or other implant material and introduce the material to an implant site. The shaft of the apparatus is shaped so as to allow the affixation of a drill guide and drill while simultaneously holding the implant material in the implant site. Various other tools include dilators and cannula that are designed to improve accessibility and efficiency in implanting the material, as well as reduce trauma to the patient, including limiting the risk of ischemic injury due to the displacement of muscle or other tissue when accessing the implant site. In addition to these tools, fastening devices such as screws and/or staples are described herein for securing the bioactive or other implant material to the implant site. One aspect of the invention is the near simultaneous implanting of material and fixation of a facet joint accomplished by using the various tools described herein. Other aspects of the present disclosure are described in detail below.

Although certain embodiments of the present disclosure may include various tools to be used with various head shapes and configurations as well as shaft lengths and shaft configurations, preferred embodiments of the present disclosure are depicted in FIGS. 3A-12F. FIG. 3A illustrates an apparatus for implanting an implantable material, preferably comprising a forked end and a passively flexible distal shaft. Further description of this apparatus in its varying embodiments is provided below.

FIG. 1A is a view of the implant site which consists of two adjacent vertebrae. As illustrated, portions of the vertebrae have been deburred and shaped in preparation for implantation. FIG. 1B is a cross sectional view of a facet joint which is the implantation site. This FIG. 1B further illustrates a facet joint that has been prepared for surgery. As can be appreciated, the tissue has been shaped to allow access to the implantation site, and allows application of a fixation device.

FIG. 2 depicts various rasps and curettes that may be used by a surgeon to remove tissue from the implant site or surrounding area and prepare the implant surface. These tools may be of varying lengths and shapes to aid the surgeon in introducing the tool to the intended site in a minimally invasive manner, such as via a cannula through a minor incision in the patient. FIG. 2 includes an illustration of one rasp with a superior abrasive surface, one rasp with an inferior abrasive surface, one curette with a superior cleaning surface, and one curette with an inferior cleaning surface. These and other tools are often used for preparing the surfaces of the vertebrae and corresponding joints prior to implanting one or more implantable materials.

According to one embodiment, an improved apparatus is disclosed for providing fixation of adjacent vertebral bodies, which comprises a handle, an elongated shaft, and a head that selectively grasps, for example, an implantable material which is adapted to be inserted into the joint space between two or more intervertebral bodies. The head of the apparatus can be any of a plurality of shapes, for example, an arcuate shaped head, where the head is asymmetrically secured to the distal shaft. Alternatively, the head may be symmetric about the point it is secured to the distal shaft.

The head may be further comprised of a variably rigid material designed to allow the bioactive material to be, for example, frictionally or mechanically held in place, and released upon application of a particular force. In another embodiment of the apparatus, the head may be made of a semi-flexible material that is capable of grasping the bioactive material and releasing the bioactive material when a particular force is applied, for example, a force in a particular dimension. Alternatively, for example, the head may be selectively capable of grasping/releasing the bioactive material once a particular torque is transmitted from the shaft to the head of the apparatus.

FIG. 3A is a side elevation view of the apparatus according to one particular embodiment of the present disclosure. As illustrated, the head of the apparatus is set at an angle. This angle aids the surgeon in introducing the bioactive material to the implant site. In a preferred embodiment the angle is fixed but according to alternate embodiments the angle is variable and may be set by the user. The proximal portion of the shaft is relatively inelastic, due in part to the fact that the apparatus also serves to brace the drill guide (as illustrated in FIG. 4A). The apparatus of FIG. 3A depicts a fixed angle head with a flexible distal shaft, which may extend approximately 4-12 inches depending on the anatomy of the patient and the area of the spine (lumbar, interbody, cervical) to be operated on.

In another embodiment of the present disclosure, the head of the apparatus is angled and/or shaped to allow ideal access and placement of the implant in the joint. For example, the angle and shape of the head relative to the shaft may be optimized for a particular implant site. The angle, for example, may be selectively variable to accommodate the anatomical orientation of the disc space or joint, or permanently affixed at such angle. This angle may further depend on the specific vertebrae that form the implant site. Since the spinal column is a curved structure, angle requirements may differ with each implant site. The angle may also depend on which side of the vertebrae the implant is occurring, whether the surgeon is right or left handed, the approach taken, etc.

FIG. 3B is a front elevation view of an embodiment of the present disclosure. This figure depicts an embodiment of the present disclosure with a forked head. The forked head comprises two tines and is sized and shaped to receive a piece of bioactive material that is also sized and shaped so as to be complementary to the forked head. One skilled in the art will appreciate that the interior surface of the tines of the forked head may have a groove or a track, and that there may be more than two tines without departing from the inventive nature of this embodiment of the disclosure. The corresponding outer surface of the bioactive material may have a groove or a track to correspond to the interior surface of the forked head. This groove or track will help secure the bioactive material in the apparatus, but still permit the bioactive material to become dislodged when it is in a desired position or when a certain force is applied to the head/shaft as described above.

In another embodiment of the present disclosure, the head may be pre-fitted with, for example, bioactive material in such a manner so that the material can be easily manipulated into the facet joint (as opposed to having to coat or infuse a membrane with bioactive material immediately prior to inserting the implant). The forked end may have a mechanism that enables it to release the material once a facet screw has secured the material in the joint. The apparatus may be constructed so that the forked end can be manipulated, by way of the flexible shaft, in at least one dimension relative to the shaft, such as by guide-wires, pivot points or similar mechanisms know in the art. The apparatus may further be constructed to permit the forked end to comprise a first orientation, wherein the bioactive material is retained by the head of the apparatus, and a second orientation, wherein the bioactive material is released from the head of the apparatus. According to this embodiment, the surgeon may selectively retain or release the bioactive material by operation of the apparatus.

According to one embodiment of the present disclosure, the head itself may be selected from one or more bioactive materials, such that the head is the implant. This bioactive implant may further comprise an absorbable band, which preferably attaches to the shaft via a resorbable hex-shaped connection. According to alternate embodiments, the head may further comprise multiple absorbable bands which assist in attaching the head to the shaft. This configuration provides an implant that is distinguishable from other spinal implants, which are made exclusively of a single type of material (e.g., bone, autographed bone, graphed, allograft bone graft, etc.) According to yet an another alternate embodiment, the bioactive implant material comprising one or more absorbable bands which attaches to the shaft via a resorbable hex-shaped connector may be provided with a instrument head that does not remain in the patient with the implant material.

FIG. 4A is a side elevation view of the cross section of the joint where the apparatus which has been placed in the implant site. The figure illustrates the head of the tool which has been inserted into the facet joint between two adjacent vertebrae. The apparatus has positioned the bioactive material ideally in the joint space to span the width of the joint. According to certain embodiments, a drill may be used to create one or more hole(s) for inserting a screw, staple, or other fastening device for assisting in retaining the bioactive membrane material. A drill hole which traverses the facet joint and the bioactive material may also serve as a conduit through which semi-liquid or liquid materials can be directly placed in contact with the biomembrane. These combined materials can stimulate the bone formation process, for example, by adding substrate such a bone morphogenic protein, platelet rich plasma concentrate, or growth hormone, directly inoculating the joint-encased membrane.

In a similar strategy, the painful small joints of the body can be so treated where amenable to fusion. One can use this strategy to fuse the interphalangeal joints of the fingers or toes by preparing the cartilage surface of the joint as describe above, and in the same endoscopic fashion applying the bioactive membrane. The drill hole can then be used to infiltrate the stimulating fusion concoction. In these types of applications a cancellous bone screw, or other fastening device may then be added through the drill hole(s) to stabilize the joint and lock the membrane in an ideal position.

FIG. 4A also depicts a drill guide which has been affixed to the stiff, proximal portion of the shaft of the apparatus. The figure further illustrates that the drill guide may be selectively positioned along the shaft of the apparatus in ideal preparation for the drill, either before the apparatus has been placed inside the patient or during the surgical procedure.

FIG. 4B is a side elevation view of the apparatus in the joint, and a drill guide which is attached to the shaft of the apparatus and has been placed adjacent to the bone and implant site, and a drill which has been placed in the drill guide. The figure illustrates how the drill guide, coupled with the apparatus, isolates the implant region and enables the drill to securely and predictably create a hole into the joint. One skilled in the art will appreciate that the drill guide and drill bit have been appropriately selected to enable a hole of a specific length and gauge to be made in both adjacent vertebrae. In order to provide adequate fixation of the two bones, it is necessary to make a hole in both adjacent vertebrae.

FIG. 4C is a side elevation view of the joint after the drill and drill guide have been removed, and after a facet screw has been inserted into the joint. The figure depicts how the screw has been assembled to the joint so as to secure the bioactive material in the joint region. The figure also depicts the apparatus still assembled to the bioactive material, and thus still located in the implant site. One skilled in the art will appreciate that the facet screw has been appropriately sized to span the width of the implant and provide adequate penetration into the adjacent vertebra to provide adequate fixation support.

Figure 5A:
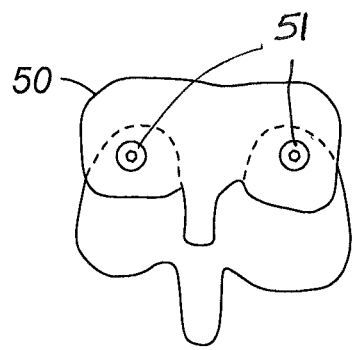
FIG. 5A is a top elevation view of two adjacent vertebrae with an implantable material and screw inserted into the joint, and with the apparatus of FIG. 3A removed from the site.

FIG. 5A is an inferior elevation view of the implant site which consists of two adjacent vertebrae. As illustrated, the facet screws have been assembled to the joint, and the apparatus has been removed from the implant site. As described above, the apparatus along with the forked head may be detached from the bioactive material and thus removed from the implant site by selectively detaching the apparatus from the material, or by passive means which may include applying a torque to the apparatus or applying force in a particular direction which separates the forked head from the bioactive material.

Figure 5B:
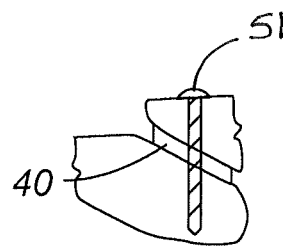
FIG. 5B is a side elevation view of the two vertebrae of FIG. 5A with the implantable material and screw inserted into the joint.

FIG. 5B is a cross sectional view of the joint after a completed implant and fixation. The figure illustrates that the drill and drill guide have been removed, a facet screw has been inserted into the joint, the apparatus has been removed, and the bioactive material has been secured in the joint. The securing of the bioactive material to the joint is in such a manner so as not to interfere with the removal of the apparatus, the forked head or other tools described herein, which further reduces the chance of trauma or ischemic injury to the patient.

According to one embodiment of the present disclosure, a method of posterior spinal fixation is provided, which includes using a device under microscopic control or loupe magnification to burr off the bottom of the facet joint. Curettes and rasps of the type described herein may be used to prepare the facet joint and to create a bleeding surface. Then the surgeon may employ a tool, preferably comprising a forked end and a flexible distal shaft, fitted with bioactive material, to inset and place the bioactive material between the leaves of the joint. Next, a drill guide is lowered over the shaft of the tool until it is adjacent to the facet joint. Then a drill is inserted through the drill guide to create hole(s) through the facet joint. A specially designed screw or other fastening device is then assembled through the hole(s) or otherwise adjacent the facet, thereby trapping the bioactive material in the joint. The forked tool is then removed, leaving the bioactive material in the joint space. This method is accomplished in a minimally invasive manner to provide near-simultaneous fixation of the vertebral bodies surrounding the facet joint.

Figure 6A:
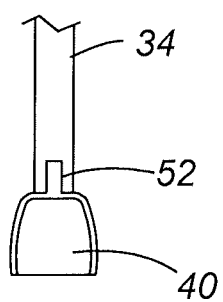
FIG. 6A is a front elevation view of an alternative embodiment of the apparatus of FIG. 3A, which illustrates the head having a partially hollow shaft that is inserted into the shaft of the apparatus.
Figure 6B:
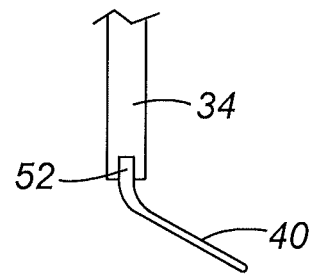
FIG. 6B is a side elevation view of the apparatus of FIG. 6A, which illustrates the head having a partially hollow shaft that is inserted into the shaft of the apparatus.

FIG. 6A is a front elevation view of an embodiment of the present disclosure. The figure illustrates an aspect of this embodiment where the entire head of the device comprises the implant material. FIG. 6B is a side aspect view of an embodiment of the present disclosure, and it further illustrates the angle between the shaft of the embodiment and the surface of the head. According to this embodiment, the head is inserted and remains in the joint after the shaft of the apparatus has been selectively detached from the head and then removed from the patient. In this orientation, the apparatus requires a connection between the shaft and the head, as opposed to the head and the bioactive material. This connection may be comprised of a pin connection, a ball and socket connection, a magnetic connection, or other similar connecting means.

Figure 7A:
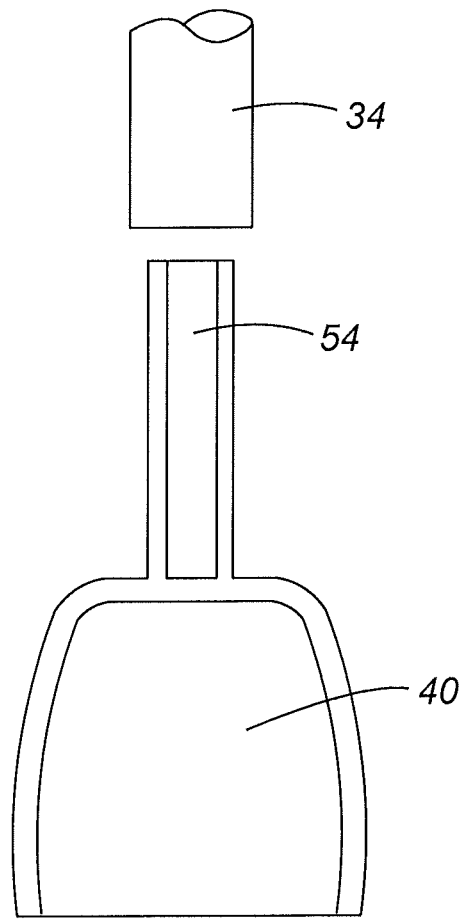
FIG. 7A is detailed front elevation view of the assembly between the head of the apparatus and the partially hollow shaft of the apparatus according to one embodiment of the present disclosure.

FIG. 7A is a front elevation view of an embodiment of the present disclosure where the entire head of the device comprises the implant material. This figure illustrates one embodiment of the present disclosure where the detachment of the head from the shaft of the apparatus is demonstrated. As illustrated, most, or substantially all of the head may be comprised of bioactive material.

Referring now to FIGS. 7A and 7B, according to this embodiment the head of the apparatus is comprised of a substantially flat, spatula-shaped component, which is in communication with a shaft connection component on a first side of the head. The shaft connection component of the head is designed such that it assembles to a distal end of the shaft of the apparatus. As illustrated in FIG. 7B, the shaft of the apparatus is manufactured with a hollow space such that the shaft component of the head assembles to the hollow space of the shaft of the apparatus. The shaft of the apparatus may, alternatively, be manufactured with a plunger that selectively pushes the shaft component of the head out of the hollow space, effectively disassembling the head from the shaft of the apparatus. One having skill in the art will appreciate that there exist other methods of selectively attaching and detaching the head from the shaft of the apparatus.

Thus, according to one embodiment of the present disclosure, the graft material for implanting into the patient may be prefabricated, and combined with a semi-rigid material. This composite material may have a hexagonal end that fits into the shaft and/or handle of the drill guide section, which allows introduction of the material into the joint and detachment of the grafting material from the introduction tool. The hexagonal end has a built-in angle corresponding to the angle of the facet joint. Preferably, the angle is approximately 45 degrees in the cervical spine, approximately 90 degrees in the thoracic spine, and approximately 180 degrees in the lumbar spine.

The prefabricated osteobiologic material and integrated tool head provides a unique combination that allows for ease of insertion and maximizes the grafting surface area. The handle portion may be an inert non-absorbable material including, for example, nylon or slowly absorbing poly gel acetate, either of which may have the attachment of biomaterial incorporated. By providing a resorbable material that attaches to the bioactive implant material, the resorbable material may also serve as a conduit for inoculation of BMP, bone marrow aspirate concentrate or other hormonal materials. The resorbable material may further provide a conduit for introducing other materials such as metabolic stimulators. The extra-articular section of the composite can be trimmed at the joint surface once the joint has been stabilized by the screw, which further secures the grafting material in place.

FIG. 7C illustrates a cross sectional view of the shaft portion of the head of the apparatus according to this embodiment. As illustrated, the shaft portion has a hexagonal shape. One having skill in the art will appreciate that the shaft of the apparatus will have a complementary hexagonal shape or other shape which assembles to the shaft of the head (see for example a twelve point socket). One having skill in the art will also appreciate that the shaft of the head need not be hexagonal in shape. It may, for example, be circular, semicircular, flat, square or triangular. The shaft of the head may also be, for example, symmetric or asymmetric. One having skill in the art will appreciate that the complementary aspect of the shaft of the apparatus will be shaped to allow the shaft of the head to assemble with the shaft of the apparatus.

FIG. 8 is a side elevation view of an embodiment of the present disclosure where the head of the apparatus is secured in the implant site, and the shaft of the apparatus is detached from the head.

FIG. 9A is a side elevation view of a facet screw and washer assembly according to one embodiment of the present disclosure, which may be used to assist in fusing the vertebrae or other aspects of the joint and the implant material. In the illustration, the facet screw has a lagged thread, which enables the selective compression of the joint region during assembly of the implant to the joint. This type of threading may not be applicable to all types of implants. One having skill in the art will appreciate that different lengths, threads, spacing and lags may be used. FIG. 9B is a top aspect view of the facet screw according to this embodiment. This illustrates a screw with a rounded, allen-type head. One having skill in the art will appreciate that the facet screw may have a head comprising other form factors. It is another aspect of the present disclosure that the screw may be hollow, having an opening at or near the head of the screw, and having at least one opening on the shaft of the screw. The openings at or near the head and on the shaft are designed to permit fluid communication between the hollow interior of the screw and the outside of the screw.

It is thus one aspect of the present disclosure that at least one opening on the shaft of the screw be positioned such that bioactive material and/or other material can be injected into the joint space or implant site by urging the material into the screw head, through the hollow interior of the screw and out the at least one opening on the shaft of the screw. One having skill in the art will appreciate that the at least one opening on the shaft of the screw may be located in a flute or flight of the threads, in the lag portion or in the tip. One having skill in the art will further appreciate the method by which an urging mechanism may be attached to the end of the screw to urge the bioactive material and/or other material into the screw. It is yet another aspect of the present disclosure that the screw is a porous material and/or comprised of a bioactive material. In still yet another aspect of the present disclosure, the screw may have a coating or impregnated with bioactive material.

In another embodiment of the present disclosure, the head of the apparatus is angled and is shaped to allow ideal access and placement of the implant in the joint. For example, the angle and shape of the head relative to the shaft may be optimized for a particular implant site. The angle, for example, may be selectively variable or affixed. This angle may further depend on the specific vertebrae that form the implant site. Since the spinal column is a curved structure, angle requirements may differ with each implant site. The angle may also depend on which side of the vertebrae the implant is occurring.

Figure 10A:
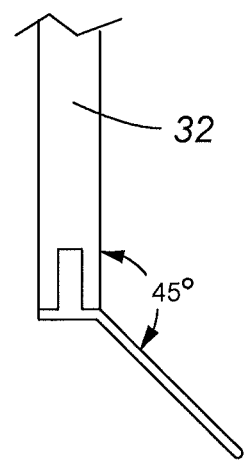
FIGS. 10A-10C are side elevation views of apparatus according to alternative embodiments of the present disclosure.
Figure 10B:
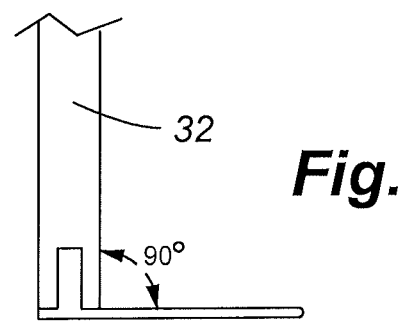
Figure 10C:
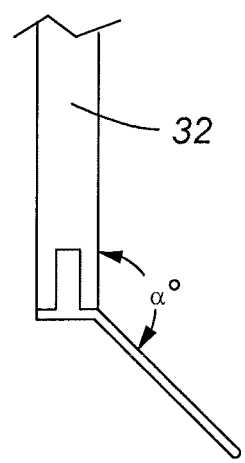
Figure 12A:
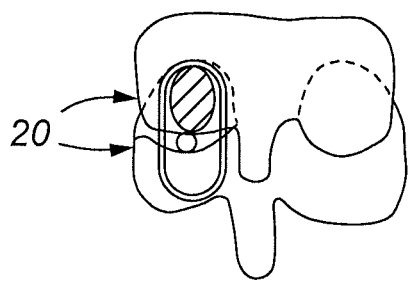
FIGS. 12A-12J are various views of fastening devices for fixation of vertebrae, along with the surgical cannula used in conjunction with certain embodiments of the present disclosure.
Figure 12B:
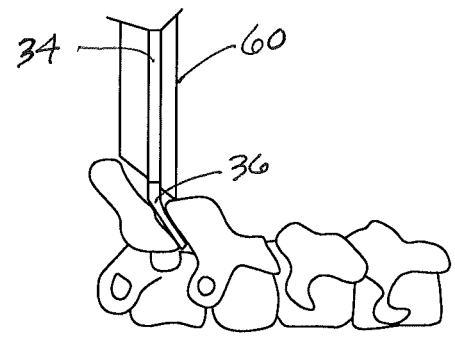
Figure 12C:
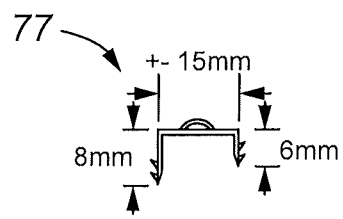
Figure 12D:
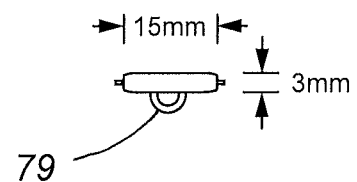
Figure 12E:
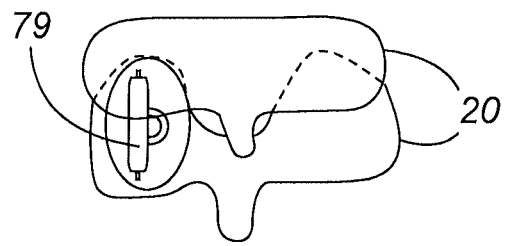
Figure 12F:
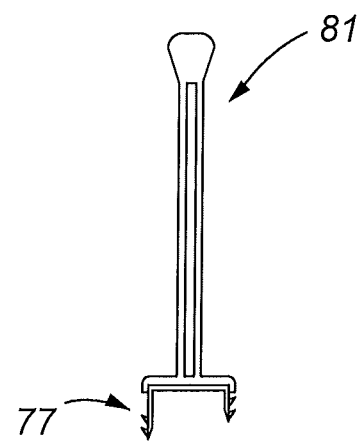
Figure 12G:
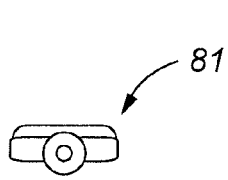
Figure 12H:
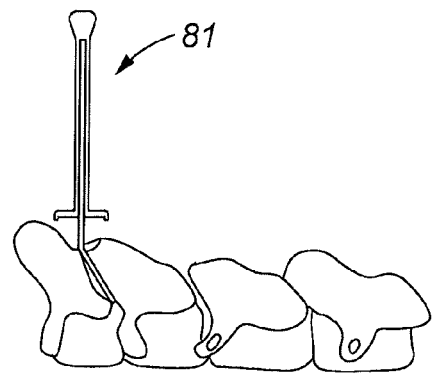
Figure 12I:
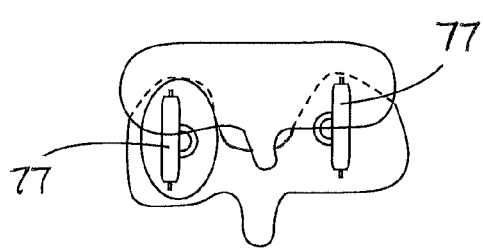
Figure 12J:
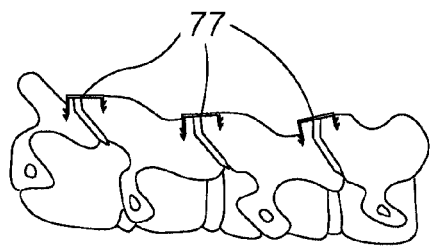

FIGS. 10A-10C are side elevation views of one embodiment of the present disclosure illustrating that the angle between the shaft of the head and the head determines the overall angle between the shaft of the apparatus and the head. The figures further illustrate that different angles may be appropriate for different joints. One having skill in the art will appreciate the bone markings and anatomy of the various vertebrae and joints, and understand the ideal angle between the shaft of the head and the head for a given procedure or surgical site. FIG. 10A illustrates, for example, that an approximately 45 degree angle may be appropriate for use in a cervical joint. FIG. 10B illustrates, for example, that an approximately 90 degree angle may be appropriate for use in a thoracic joint. FIG. 10C illustrates, for example, that an approximate 180 degree angle may be appropriate for use in a lumbar joint. FIGS. 10a-10c taken together illustrate another aspect of the present disclosure, which is that the shaft of the apparatus may be applied in several different implant scenarios, and that only the head of the apparatus needs to be appropriately selected.

Another unique tool in the present disclosure is a cannula having a shape other than round (e.g., oval, pointed, square cornered, etc.) and having an end (e.g., the end inserted into the patient, distal from the user) that is angled and/or shaped to be ideally seated in a surgical site. Asymmetrical cannulas may allow visualization of the facet joint (DePuy has apparently described oval cannulas). An "egg-shaped" cross section may allow for the best view of the facet joint and minimizes the medial-lateral dissection that a round cannula would require.

Still other aspects of the invention are directed to cannula instruments that have a patient contacting end that is adjustable to assume a predetermined conformation. Thus, in one embodiment, material forms the tip end that comes into contact with bone, tissue, and particularly near especially nerve tissue, with such cannula end material being malleable to an extent necessary for the surgeon to mold the end conformation such that it achieves desired avoidance of particular structures encountered in any particular surgery. Thus, if a bony outcropping, a nerve fiber, etc. is perceived by the surgeon, the cannula tip end can be adjusted to avoid undesired contact or interference with such tissues or structures. In particular embodiments, the ability to adjust the geometric parameters of the tip end is achieved by manipulation of the other end of the instrument. For example, providing a turnable component at the opposite end of the instrument, the shape of the other end of the instrument (i.e. the end inserted into the patient) can be adjusted to expand circumference, reduce circumference, render the opening more or less oblong, etc. In such a manner, it is possible to avoid having to remove the instrument or cannula from the patient's site to adjust the morphology of the instrument or cannula operating end, thus saving time, avoiding undesired reinsertion procedures, etc.

FIGS. 11A-11F are various views of certain embodiments of a surgical cannula that may be used in conjunction with certain aspects of the present disclosure. FIGS. 11A and 11B show side elevation views of certain embodiment of the cannula 60 and 62 respectively. FIG. 11A shows the cannula 60 having a bottom opening that is angled oblique to the top opening. FIG. 11B shows the cannula 62 having a bottom opening that is substantially parallel to the top opening. FIG. 11C shows a top aspect view of the cannula 64. The figure shows the cannula 64 having an elliptical cross-section. In one embodiment, the ellipse has a width of 20 millimeters in its major axis, and a width of 16 millimeters in its minor axis. It will be appreciated that the cannula cross-section may be of a different size and have a different shape including, for example, an oval, a rectangle, a square, a rhombus, a trapezoid, a parallelogram, a polygon and a generally oblong shape. As will be appreciated by one having skill in the art, the cross-sectional shape of the cannula 60 permits the user to employ instruments in the cannula that require movement or manipulation in one direction, preferably along the major axis, but to a lesser extent in the other direction. The oblong shape of the cannula 60 would permit, for example, the rasps and curettes in FIG. 2 to be manipulated and used in a joint in a minimally invasive fashion. Similarly, the tool 32 can be manipulated and used in a joint even with the head 36 at any angle relative to the shaft. One having skill in the art will appreciate that the dimensional requirements of the cannula 60 will vary based on the length of the cannula, and the items or tools being inserted therein.

FIG. 11D shows two vertebrae 20 and a view of the footprint made by a cannula 60 in one embodiment of the present disclosure. As will be appreciated, the cannula 60 provides access to adjacent facets of two adjacent vertebrae. The oval or elliptical shape of the cannula 60, however, allows the procedure to be performed in a minimally invasive fashion by reducing the incision required to gain access to the surgical site and the reducing the tissue exposed during the procedure. FIG. 11E is a side aspect view of the cannula 60 placed over two adjacent bones 20 separated by a joint space. The view in FIG. 11E is the side aspect view of the cannula 60 in, for example, FIG. 11D. FIG. 11E exemplifies another advantage provided by certain embodiments of the cannula 60 in the present disclosure in that it provides optimal access to a surgical site that may have anatomy or bone features that make it desirable to have, for example, an angled and/or curved end to the cannula. One having skill in the art will further appreciate that an ideally shaped cannula 60 will allow the user to more safely and reliably access the surgical site and will reduce the risk of injury to the surrounding tissue.

FIG. 11F shows the shaft and cross-sectional or end views of various dilators 66. The various dilators 66 shown are of various sizes, having various lengths and cross-sectional areas. As can be seen by the cross-sectional or end view of the dilators 66, the dilators 66, like the cannulae described above have an oval or elliptical shape. According to a preferred embodiment, one or more dilators may be used to dilate the muscle or other tissue of the patient to access the surgical site. A first slender dilator 66 is used to probe through the muscle or other tissue and to locate the desired vertebrae. Once that first slender dilator 66 is seated, additional dilators 66 may be inserted around the previously seated dilator 66 until the desired circumference through the muscle or other tissue is achieved. In this fashion, the first slender dilator 66 serves as a radiographic marker, and establishes the path for subsequent dilators 66 of greater circumference than the first slender dilator 66. This serves to reduce ischemic injury to the patient and reduces the time necessary to locate and access the desired vertebrae. The first slender dilator 66 has a sufficient circumference to be easily viewed by x-ray or other imaging technology when seating the dilator 66 on the desired vertebrae. The dilators 66 are variable in length, preferably ranging from 3-14 cm.

Once the dilators 66 have been used to dilate the muscle tissue surrounding the path to the desired vertebrae, a cannula 60 may be inserted into the interior circumference of the dilators 66. The cannula 60 according to a preferred embodiment is ovoid in shape to permit dissection from caudad to cephalad (as opposed to from medial to lateral) and further accommodate dissection about the facet joint. As with the dilators 66, the cannula 60 may be variable in length, ranging preferably from 3-10 cm, to accommodate varying depths from skin to bone. As mentioned above, the cross-sectional geometry of the cannula is preferably ovoid in shape, and in a preferred embodiment the major diametrical axis of the cannula is about 20 mm, and the minor diametrical axis of the cannula is about 16 mm.

Varying embodiments of the cannula described herein may further comprise an angled or sloped surface at one distal end of the cannula for accommodating access and viewing of an implant site that is not directly below the incision. By way of example but not limitation, a surgeon may use one or more of the angled cannula shown in FIGS. 11A-11F in conjunction with the dilators 66 described herein to probe through the muscle or other tissue using an angled approach, thereby allowing access to a specific vertebrae either above or below the vertebrae directly below the incision. Once the dilators have been used to clear a path through the muscle or other tissue at an angled approach, the angled cannula may be inserted with the angled or sloped surface oriented so that the angled or sloped surface rests near horizontally against the vertebrae, as shown in the appended Figures. This angled cannula assists the access and visibility of additional vertebrae without requiring additional incisions, and further permits securing fastening devices such as screws using an angled approach. As with the other cannula described above, the cross-sectional shape of the angled cannula is preferably ovoid in shape, and the entire longitudinal length of the angled cannula may be slightly greater than the other cannula described herein.

Thus, according to one embodiment of the present disclosure, a method for fusing one or more facet joints is disclosed, whereby a surgeon may use the dilators and cannula described in the preceding paragraphs to access a first facet joint, nearly directly underneath the incision, and in particular by using the straight surfaced cannula described above. Once the joint has been treated, the cannula may be removed and the dilators 66 used again but now using an angled approach through the muscle or other tissue to access a different facet joint. Once the first dilator 66 has located the desired facet joint, additional dilators may be employed to enlarge the path through the muscle or other tissue, and ultimately the angled cannula inserted through the path to the implant site. Once the second facet joint has been treated the angled cannula may be removed, and the steps described above repeated to access additional facet joints. In this fashion a multi-level fusion may be accomplished without the need for additional incision, and still permit the surgeon to achieve a wide viewing area along the surface of the vertebrae, wherein the angled or sloped surface of the angled cannula rests nearly horizontally about the surface of the vertebrae.

Referring now to FIGS. 12A-12F, another method for stabilizing the facet joints of the spine utilizing a minimally invasive approach involves the same cannula exposure and application of the bioactive membrane. Measurements suggest the size of the membrane is on average 9×6 mm in size. The handle or shaft used to direct the membrane into position is hexagonal in cross-section and has a 3 mm perimeter. Once the graft is in position, an asymmetric, barbed staple is placed over the shaft so that it covers the tab of the bioactive membrane. The staple is attached to an impactor which controls the rotation of the staple and ensures uniform impaction into the bone. The position of the membrane tag and resultant position of the shaft help determine the position of the staple which is impacted into both leaves of the facet joint.

According to an alternate embodiment, a staple, clamp, hook, or other fastening device may be used for retaining the implant within the facet, either in addition to or in lieu of a facet screw. The staple may be made of a spring metal. When in its relaxed posture, the staple's top surface is curved, which angles the asymmetric legs towards one another. When the spring metal staple is placed in its holder, it flattens out the surface of the staple and the staple legs return to near right angles. Once the staple is impacted, it tries to return to its relaxed position, which has the effect of compressing the leaves of the facet joint against the bioactive implant. In another aspect of the design, the staple is made of a memory metal, such as nytenol. At room temperature it's legs are at near right angles to its surface. At body temperature, the surface of the staple attempts to bend, which drives the legs of the staple together. Once implanted, and as the staple warms, it converts to a compressive loading device.

The staple described according to this embodiment preferably measures 15 mm in length, its cephalic end having at least one barb and about 6 mm in length, its caudal end also having at least one barb and about 8 mm in length. Preferably the staples have at least two barbs on each of the cephalic and caudal end. The view from the top shows a generally asymmetric collar attached to the staple. The collar allows positioning of the staple over the tab of the bioactive membrane which helps hold it in place. The asymmetry of the staple legs is necessary to conform the staple to the peak of the bony contours of the facet joints, where the superior leaf is a peak, and the inferior leaf is a valley. The asymmetric collar on the staple helps to direct the staple more laterally, where the bone is thicker and further away from the spinal cord. One advantage of this method and apparatus is that it simplifies the fixation of the joint, and avoids having to change or reorient the cannula to apply a drill hole or screw. This method further eliminates risk of overdrilling or cracking of the bone due to the length or thickness of the screw.

According to another embodiment, the staple is not secured at all to the bioactive membrane. In yet another embodiment, the bioactive membrane may be permanently attached to the staple, or packaged with the staple as a unit for implanting and fixating the implant material in the joint. The staple may have two barbs of the same length, or with one barb being slightly longer than the other barb to accommodate for the anatomy of the patient's adjoining facets. Various staples may be used with this apparatus and method, including staples comprising a series of barbs as opposed to two individual barbs on either end of a collar. According to yet another embodiment, an inserter may be provided with two "feet" at one distal end that allows the staple to attach temporarily to the inserter by placing the "feet" on the collar and between the barbs of the staple. In this manner, the inserter may be used in conjunction with the forked tool for implanting the bioactive material, or may be placed around the outer circumference of the forked tool to allow the implant and fixation to occur nearly simultaneously. In yet another embodiment, the "feet" may be incorporated in the shaft of the forked tool, thereby eliminating the need for two separate tools within the narrow cannula.

Figure 13D:
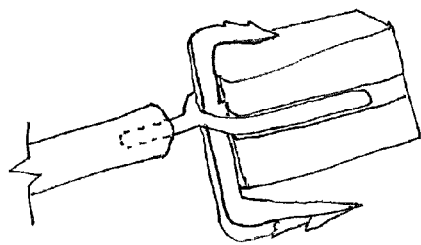
FIGS. 13A-13D are views of a fastening device for fixation of vertebrae, along with the apparatus and implant of FIG. 3B.
Figure 13C:
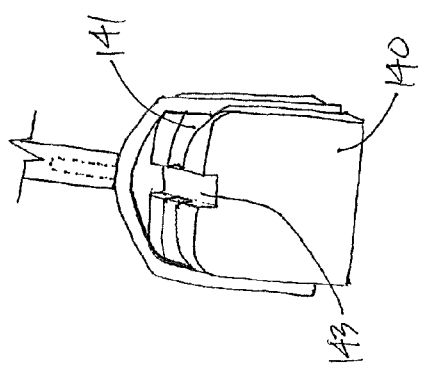
Figure 13B:
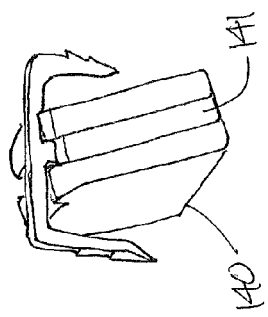
Figure 13A:
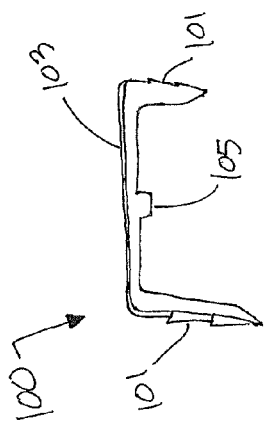

Referring now in detail to FIGS. 13A-13D, a fastening device according to one embodiment of the present disclosure is shown. In FIG. 13A, an asymmetrical staple is shown, having two legs, each leg having two barbs, and the central portion of the staple between the two legs comprising a tab. Referring now to FIG. 13B, the tab may be inserted into a slot in the bioactive material described above, for inserting the staple and bioactive material simultaneously using a single tool. As shown in FIG. 13C, the tool may be comprised of a forked end, with two tines which engage a lateral slot on either side of the bioactive material. The horizontal slot shown in FIG. 13C is reserved for engagement of staple, and in particular the tab of the staple shown in FIG. 13A. Referring now to FIG. 13D, the tool, staple, and bioactive material are shown as one assembled unit. According to this embodiment, a single tool may secure both the asymmetrical staple, and the bioactive material, prior to insertion and delivery to the surgical site. This permits a surgeon to insert a single tool, which provides the bioactive material to the disc space or facet joint, and simultaneously position the asymmetrical staple on either side of the facet joint. Once the bioactive material and staple are in place an additional tool may be inserted to drive the two legs of the staple into either predrilled holes or directly to the surfaces of the vertebrae adjacent the facet joint. Once the staple is secured, it holds the bioactive material in place, and the tool may be removed without disturbing either the bioactive material or the asymmetrical staple.

According to varying embodiments, the asymmetrical staple described herein may be comprised of a variety of different materials. For example, the staple may be made of a spring metal, which has certain compressive properties, or that is substantially rigid yet flexible to secure the bioactive material in the facet joint despite movement of the intervertebral bodies surrounding the joint. According to another embodiment, the staple may be formed of a memory metal, for example, nytenol, which also exerts a compressive force within the joint. Memory metal also has the advantage of being able to adjust to the particular anatomy of the patient, the movement of the vertebrae, the distortion of the staple during insertion and implant of the bioactive material, and to the bioactive material itself as it fuses with the vertebrae. This is particularly beneficial when some or all of the implant is made from a resorbable material.

According to yet another embodiment, the staple shown in FIGS. 13A-13D may be substantially hollow such that a fast curing epoxy or cement, a fast curing bioactive cement, a cell culture, or other biologically inert substance may be injected into the substantially hollow staple via the shaft of the tool, and then ejected out one or more openings at the distal end of each of the legs of staple shown in FIG. 13A. According to yet another embodiment of the present disclosure, the staple may be made of a variety of materials, such as demineralized bone matrix, a flexible collagenous polymer, a semi-solid putty, or a viscoelastic matrix. In yet other embodiments the staple may be made of a common material such as stainless steal, titanium alloy, aluminum alloy, chromium alloy, or other metal or metal alloys. Material that the staple is comprised of may also include, for example, PEEK, carbon fiber, ABS plastic, polyurethane, rubber, latex, synthetic rubber, and/or other fiber incased resinous materials, synthetic materials, polymers, and natural materials, either in whole or in part. The hollow design allows for virtual filling of the staple and/or the pre-drilled holes and/or portions of the joint with the resulting increase in the chance for fusion.

Referring now to FIGS. 14A-14B, a staple for securing adjacent vertebrae in the lumbar spine region is shown. FIG. 14A shows a top perspective view of a lumbar staple, which comprises a substantially planar bridge, further comprising a central aperture, and four legs positioned approximately at each corner of the substantially planar bridge. The central aperture allows insertion and application of a tool, such as the one referred to above in respect to FIGS. 13A-13D. The central aperture also permits the insertion of a tamp or other tool after the insertion tool of FIGS. 13A-13D has been removed. In a preferred embodiment, the lumbar staple has four legs, each comprising at least two barbs, although in alternate embodiments more or fewer barbs and/or fewer or more legs may be used. Referring now to FIG. 14B, a side perspective view of the lumbar staple of FIG. 14A is shown. As shown in FIGS. 14A and 14B, the lumbar staple further comprises a collar for coupling to the shaft of an apparatus for introducing the staple simultaneously with the bioactive material or other implant, and that permits the shaft of the apparatus to disengage the staple once it is positioned in the joint.

Similar to the asymmetrical staple of FIGS. 13A-13D, the lumbar staple may be made of a variety of different materials, including spring metal, memory metal (e.g., nytenol), or any of the other materials referenced above in connection to the asymmetrical staple. The method of simultaneously inserting the staple and the bioactive material or other implant described above in relation to FIGS. 13A-13D also applies for the lumbar staple shown in FIGS. 14A-14B.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An apparatus for providing fixation of adjacent vertebral bodies comprising:
   a handle;
   an elongated shaft;
   a head coupled to the elongated shaft;
   wherein the head further comprises a forked end having two or more tines for grasping a bioactive implantable material which is adapted to be inserted into the joint space between two or more intervertebral bodies, wherein each of said two or more tines are free-standing with a first proximal end and a second distal end, wherein said second distal end is not connected to a distal end of another of said two or more tines; and
   wherein the elongated shaft further comprises a generally cylindrical body having a continuous, hollow portion about a longitudinal axis of the generally cylindrical body, which is in communication with at least one aperture located at the distal end of the elongated shaft; and
   wherein said head is composed of bioactive implant material.

2. The apparatus according to claim 1 wherein the head is connected to the shaft of the apparatus by connecting means, the connecting means comprising means for selectively attaching and removing the head from the shaft.

3. The apparatus according to claim 2 wherein the connecting means is comprised of a pinned connection.

4. The apparatus according to claim 1 wherein said elongated shaft is angled at 45°.

5. The apparatus according to claim 1, wherein the implant material comprises a bioactive material in combination with a non-absorbable material.

6. The apparatus according to claim 1, wherein said forked end has two tines.

7. The apparatus according to claim 1, wherein said elongated shaft is comprised of a flexible shaft.

8. The apparatus according to claim 1, wherein said head is made of a semi-flexible material.

9. An apparatus for providing fixation of adjacent vertebral bodies comprising:
   a handle;
   an elongated shaft;
   a head coupled to the elongated shaft;
   wherein the head further comprises a forked end having two or more tines for grasping a bioactive implantable material which is adapted to be inserted into the joint space between two or more intervertebral bodies, wherein each of said two or more tines are free-standing with a first proximal end and a second distal end, wherein said second distal end is not connected to a distal end of another of said two or more tines; and
   wherein the elongated shaft further comprises a generally cylindrical body having a continuous, hollow portion about a longitudinal axis of the generally cylindrical body, which is in communication with at least one aperture located at the distal end of the elongated shaft;
   wherein the head is connected to the shaft of the apparatus by connecting means, the connecting means comprising means for selectively attaching and removing the head from the shaft; and
   wherein said connecting means comprises a vacuum or magnets.

10. The apparatus according to claim 9, wherein said elongated shaft is angled at 45°.

11. The apparatus according to claim 9, wherein the implantable material comprises a bioactive material in combination with a non-absorbable material.

12. The apparatus according to claim 9, wherein said forked end has two tines.

13. The apparatus according to claim 9, wherein said elongated shaft is comprised of a flexible shaft.

14. The apparatus according to claim 9, wherein said head is made of a semi-flexible material.

* * * * *